United States Patent

Kandel et al.

Patent Number: 5,908,394
Date of Patent: Jun. 1, 1999

[54] METHOD AND APPARATUS FOR NONINVASIVE DETERMINATION OF A DISEASE STATE OF A HUMAN EYE

[75] Inventors: Gillray L. Kandel, Troy; John Schroeder, Schenectady, both of N.Y.

[73] Assignee: Ronsselaer Polytechnic Institute, Troy, N.Y.

[21] Appl. No.: 09/022,147

[22] Filed: Feb. 11, 1998

Related U.S. Application Data

[63] Continuation-in-part of application No. 08/814,595, Mar. 10, 1997, abandoned, which is a continuation of application No. 08/477,314, Jun. 7, 1995, Pat. No. 5,609,159.

[51] Int. Cl.⁶ .................................................. A61B 13/00
[52] U.S. Cl. .......................................................... 600/558
[58] Field of Search .................... 600/558; 351/213–215, 351/221

[56] References Cited

U.S. PATENT DOCUMENTS

| | | | |
|---|---|---|---|
| 3,947,099 | 3/1976 | Grolman et al. | 351/35 |
| 4,711,542 | 12/1987 | Ichihashi et al. | 351/221 |
| 4,776,687 | 10/1988 | Nakanishi et al. | 351/214 |
| 4,863,261 | 9/1989 | Flammer | 351/221 |
| 4,993,827 | 2/1991 | Benedek et al. | 351/221 |
| 5,072,731 | 12/1991 | Taratuta et al. | 128/633 |
| 5,139,022 | 8/1992 | Lempert | 128/633 |
| 5,297,559 | 3/1994 | Severns | 128/745 |

OTHER PUBLICATIONS

Chang, Y. Ingling, C. Evaluation of the Moreland Color Match as an Indication of Retinal Pathology IEEE 9th Annual Conference of the Engineering in Medicine and Biology Society 1987.

T.P. Piantanida A Portable Filter Anomaloscope Optical Engineering vol. 15 No. 4, pp. 325–327, Jul.–Aug. 1976.

*Primary Examiner*—Max Hindenburg
*Attorney, Agent, or Firm*—Heslin & Rothenberg, P.C.

[57] ABSTRACT

To determine a cataract or the degree of cataractogenesis in an eye of a patient, the patient views two lights juxtaposed, wherein each light comprises a mixture of two different wavelength lights. One of the lights is a fixed reference mixture, while the mixture of the other non-fixed light is varied until the patient observes less distinction between the two light mixtures in terms of brightness, hue or saturation. The luminance levels of the light components of both light mixtures for providing comparison and the ratio levels of the components are predetermined. Once a transition range is established from the comparison, the predetermined ratios are then related to respective ratios of a standardized group. Deviations between the ratios of the patient and the standardized group indicate the existence of a cataract and/or the degree of a cataract precursor formation.

30 Claims, 15 Drawing Sheets

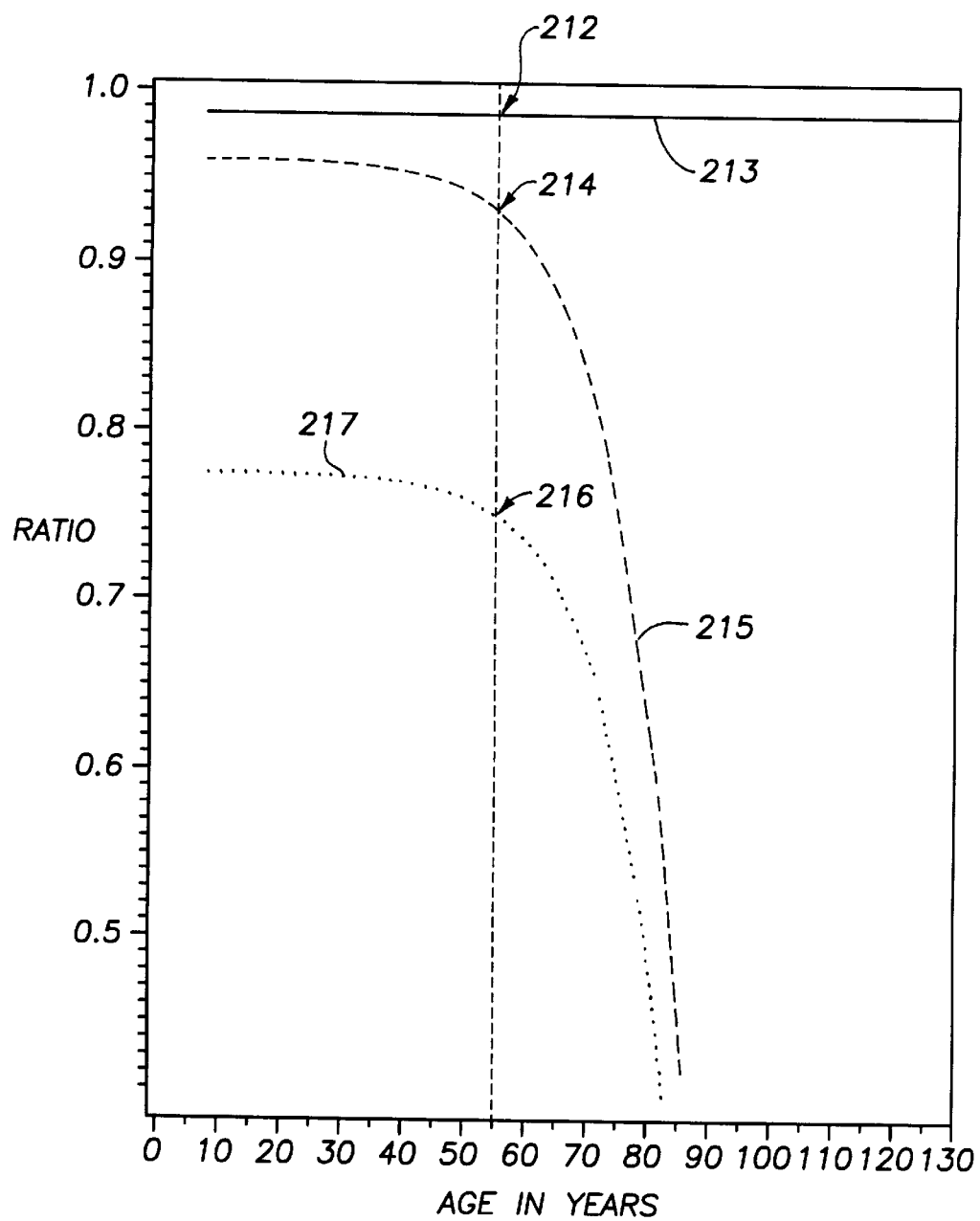

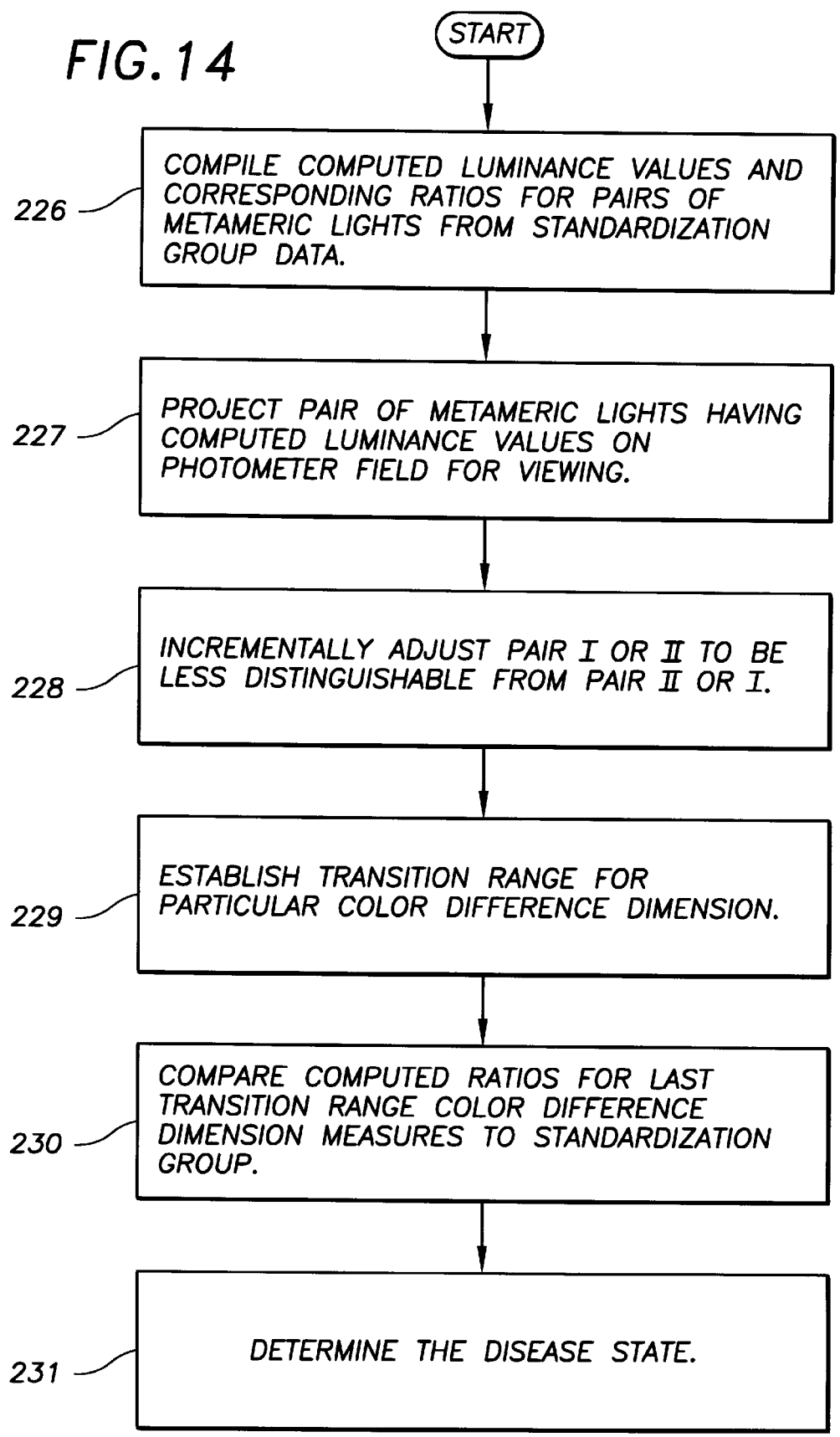

METHOD AND APPARATUS FOR NONINVASIVE DETERMINATION OF A DISEASE STATE OF A HUMAN EYE

CONTINUING DATA

This application is a continuation in part of U.S. patent application Ser. No. 08/814,595 filed Mar. 10, 1997, now abandoned which is a continuation of U.S. patent application Ser. No. 08/477,314 filed Jun. 7, 1995, now U.S. Pat. No. 5,609,159, both of which are incorporated herein by reference.

TECHNICAL FIELD

The present invention generally relates to noninvasive determination of disease states. More particularly, the present invention relates to a method and apparatus for noninvasively determining an ocular disease state, and for noninvasively determining the rate of development of this ocular disease state.

BACKGROUND ART

A person with a mature cataract, which significantly impairs visual function, can generally be treated by surgically extracting the impaired lens of the person and replacing it with either an intraocular lens or an extraocular lens. However, the condition cannot be addressed until properly diagnosed or determined.

Many different methods and apparatus have been developed in the past to help determine the existence or extent of a cataract. These methods and apparatus have generally made the determination based either on visual acuity tests or on an analysis of light exiting the eye of the patient. However, these may not be optimum indicators of a cataract, due to various anomalies. In the case of visual acuity tests, that depend upon light reaching the retina, the use of high contrast letters or figures may enable the patient to recognize the letters and figures and thus "pass" the visual acuity test regardless of a cataract condition.

Similarly, in another test which compares a photograph of a person's lens to a standardized series of photographs of a lens with different degrees of cataract formation in different parts of the lens, the resulting photographic images depend upon back scattered light from the lens. Because the back scattered light may not correlate highly with the location of the cataract and what the patient sees, a clinician using the photographs as the basis of an analysis will not be able to accurately determine the effect of opacities upon the patient's visual function and accordingly the patient may "pass" or may "fail" the test incorrectly. Moreover, in U.S. Pat. No. 4,863,261, issued to J. Flammer, entitled "Method of and Apparatus for Measuring the Extent of Clouding of the Lens of a Human Eye," light exiting the eye, i.e. "back scattered" light, is analyzed with respect to incident radiation to determine the extent of clouding of the lens.

Benedek et al., in U.S. Pat. No. 4,993,827 for "Method for Detecting Cataractogenesis", issued Feb. 19, 1991, collect and determine the intensity of light scattered from a measurement location in the lens and compares this value to the intensity of light scattered by a normal, clear lens to determine the degree of cataractogenesis at the specific measurement location.

Taratuta et al., in U.S. Pat. No. 5,072,731 for "Apparatus for Detecting Cataractogenesis Using Quasielastic Light Scattering", issued Dec. 17, 1991, analyze the light scattered from the lens using an autocorelation function or the power spectrum to separate the light fluctuation into two components: one caused by fast diffusing proteins and one caused by slow diffusing protein aggregates. The data is then compared to reference curves to determine the degree of cataractogenesis.

In each of the above back scattering techniques, low intensity light must be incident upon the eye in order to avoid damage to the eye. Of the low intensity incident light, a portion thereof is reflected for analysis. Because of the limited incident intensity, only a small amount of light is reflected back to a photomultiplier of limited quantum efficiency for measurement. The limited amount of reflected light and limited quantum efficiency of the photomultiplier make accurate analysis difficult.

Thus, a need exists for an improved, noninvasive, ocular disease state determination. The present invention meets this need by assessing the light that reaches the patient's retina and forms the proximal stimulus that the patient's visual system uses in the first stage of the perceptual process. The through-put quality of the axial portion of the lens is thereby measured indirectly by using the patient's visual system as a visual null indicator that enables one to track the rate of cataract formation. Use of the patient's retina itself as the detector provides a system of inherently superb quantum efficiency in contrast to that of known photomultipliers.

Use of the patient's own retina as a detector, moreover, permits the design of an instrument and a method that employs light of higher energy, of far shorter wavelength, e.g. 407 nm, during testing of the patient's eye. This shorter wavelength light, which enters the patient's eye, enables assessment of optical properties and characteristics of particles of sizes far smaller than those able to be characterized by the use of laser light of 633 nm wavelength.

DISCLOSURE OF THE INVENTION

Briefly, the present invention satisfies the above needs by providing a method and apparatus enabling ocular disease state determination based on light entering the patient's eye as the patient goes through a series of exercises to produce either an exact color match or some degree of distinction between different light mixtures in terms of hue, brightness or saturation.

The present invention provides, in a first aspect, a method for determining a disease state in an eye of a patient. The method comprises providing a plurality of specific monochromatic lights for viewing by the patient, observing the patient's color matching behavior for the plurality of lights and determining the extent of the disease state based upon the patient's color matching behavior. The color matches reflect the visual perceptions of the patient in accordance with the transmissive characteristics of the patient's own eye, and in particular, the lens of the patient's eye.

In a preferred embodiment of this first aspect of the present invention, each light of the plurality of the lights includes a mixture of two different wavelength lights and at least one of the light mixtures is varied as the patient's color matching behavior is observed. The step of determining the disease state may comprise determining an existence of the disease, or it may comprise determining a severity or stage of development thereof.

The present invention provides, in a second aspect, an apparatus for assisting in the determination of a disease state in an eye of a patient. The apparatus comprises a plurality of light sources and associated filters, wherein each filter passes only a narrow range of light of the associated light source about a particular wavelength. A plurality of variable light attenuators are disposed in the optical path of the respective filters for attenuating the associated filtered light. Additive mixers combine light as attenuated by given attenuators. Subsequent variable attenuators attenuate the combined light provided by the additive mixers to provide resulting light mixtures of desired brightness. The resulting lights are directed to respective portions of a photometer field adjacent to one another so that a patient may compare the individual resulting light mixtures with respect to one another. Preferably, a chopper is provided in the light paths of the individual light mixtures in alternating sequence such that the light mixtures are received at the photometer field sequentially one at a time. A controller of the apparatus enables the various light components of the mixtures to be adjusted for effecting luminance levels of the associated filtered light components as provided, in the resulting light mixtures, to the photometer field. Finally, a radiometer is included for measuring the power levels of the lights as presented to the patient within the photometer field.

In a third aspect of the present invention, a method is provided for determining a disease state in an eye of a patient in accordance with the patient's color matching behavior per different light polarizations. A first light mixture of first and second wavelength light components is matched to a second light mixture of first and second light components as observed by the patient under test, wherein the first wavelength light component of the first light mixture is of a first polarization state. The polarization state of the first wavelength light component of the first light mixture is then changed and the light ratio of the first light mixture adjusted again until attaining a match between the first and second light mixtures as perceived by the patient. The respective levels of the light components between the first match and the second match are analyzed for determining the disease state of the eye.

In a fourth aspect of the present invention, a method is provided for determining a disease state in an eye of a patient in accordance with the patient's ability to appreciate a difference between a pair of lights. A first step is to provide at least two lights for viewing by the patient, each of the lights having an associated color difference dimension. Then the patient compares a color difference dimension first measure of a principal light of the plurality of lights with a color difference dimension second measure of a select light of the plurality of lights. The select light is adjusted to make the color difference dimension second measure appear less distinguishable from the color difference dimension first measure. A disease state can then be determined based on a transition range defined by a change between the color difference dimension second and first measures.

In accordance with the above, it is an advantage of the present invention to provide a noninvasive method for determining ocular disease states.

It is another advantage of the present invention to utilize the patient's own perceptions of light in determining ocular disease states whereby the patient acts as a null indicator.

It is yet another advantage of the present invention to provide a method and an instrument to assess the precursor to cataract formation in the eye of a patient.

It is yet another advantage of the present invention to provide a method and an instrument to enable the assessment of efficacy of any cataract treatment and to estimate by how many years a non-surgical cataract treatment (medical) has delayed cataract onset.

It is a further advantage of the present invention to provide a method and an instrument to detect risk factors which promote cataract formation.

It is still another advantage of the present invention to provide quantitative analysis of a patient's judgement of light equality between additive light mixtures to determine ocular disease states.

It is yet a further advantage of the present invention to provide another method to enable the assessment of a disease state in a quick and efficient manner and which reduces the effects of a patient's subjective determination when required to determine exact matches.

BRIEF DESCRIPTION OF THE DRAWINGS

These, and other features and advantages of this invention will become apparent from the following detailed description of the various aspects of the invention taken in conjunction with the accompanying drawings.

FIG. 13 is a graph representing a compilation of predetermined luminance ratios calculated from "real" match points for a group of European-Caucasians as a standardization group; and FIG. 14 is a flow chart illustrating another method in accordance with the present invention for determining a disease state in an eye of a patient.

BEST MODE FOR CARRYING OUT THE INVENTION

Figure 1:
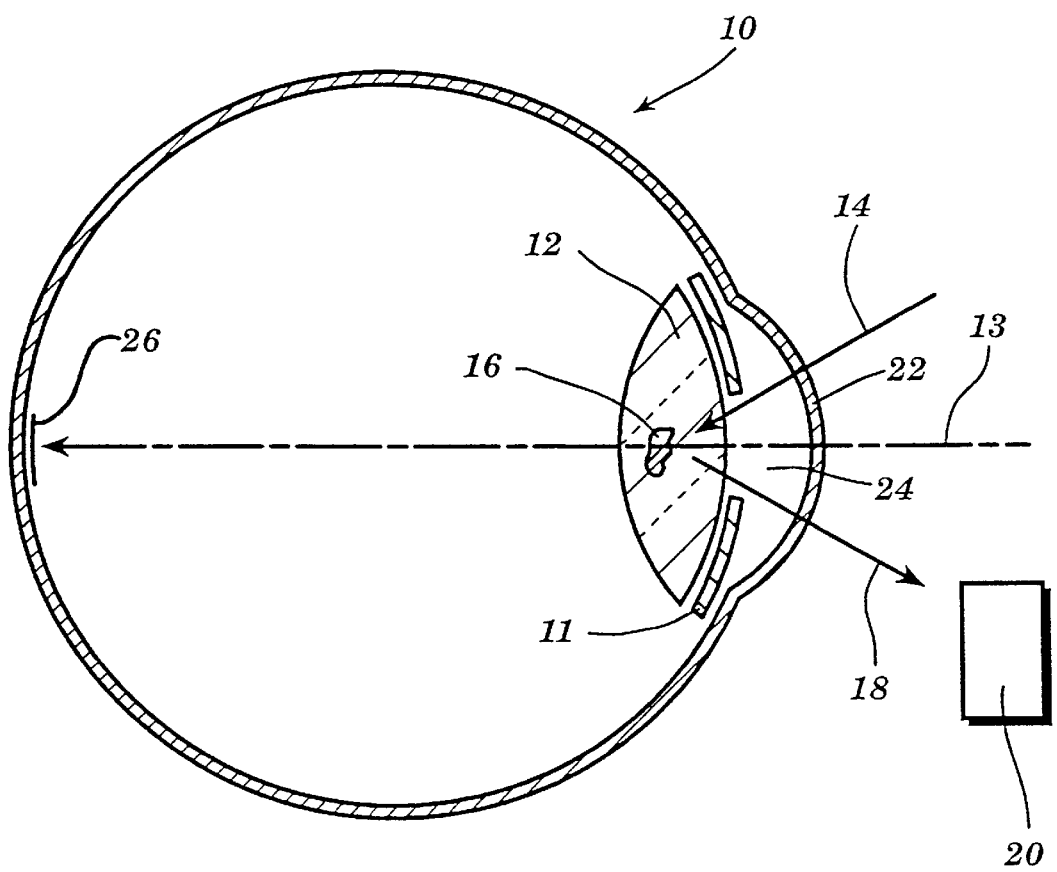
FIG. 1 depicts a light ray entering an eye and a backscattered ray exiting therefrom.

With reference to FIG. 1, a primarily spherical human eye 10 has macula region of retina 26 at the internal rear surface of eye 10 and cornea 22 provided at a forward circular region of eye 10. Crystalline lens 12 is disposed just behind the cornea 22 with aqueous humor 24 therebetween. In the absence of a cataractous condition, the human in vivo crystalline lens 12 is relatively transparent. A cataract is defined as opacification of the crystalline lens that affects visual function. This opacification is thought to result from changes in the molecular structure of the lens tissue. Except for those cataracts that result from certain systemic or traumatic insult to the lens, the progression of senile cataract (senile cataractogenesis) in humans is slow and most of these cataracts become manifest as much as two decades before the death of a person (i.e. of an average life span expectancy).

Incident light ray 14 (of FIG. 1) enters cornea 22 at the front of eye 10, passes through aqueous humor 24 and to crystalline lens 12. Iris 11 provides an aperture that limits the area of lens 12 available for passing received light. Backscattering particle 16 causes a portion 18 of the incident light to return to and exit the front of eye 10. In the past, cataract indicators have taken a generalized form of measurement device 20, which measures the amount of backscattered light 18 for determining the transparency (altered molecular structure) of crystalline lens 12. In a backscatter measurement, incident ray 14 passes through cornea 22 and aqueous humor 24 before reaching a given depth of the lens itself as associated with the backscattering. After deflection, the backscattered light passes through the same path before reaching indicator 20. Note that the backscattering measurements do not necessarily reveal anything directly about the characteristics of the light that reaches the macula retina 26 and hence can reveal little regarding the degree of visual impairment produced by an incipient cataract.

Harding, J., "Cataract: Biochemistry, Epidemiology and Pharmacology", p. 83 (Chapman and Hall, London, 1991) defines cataracts as lens opacities that adversely affect visual function. Opacities that do not affect visual function are classified solely as lens opacities. The latter are usually found in the peripheral or equatorial regions of older lenses.

In general, to maintain standard visual function, the intensity and direction of a ray of light as it passes through the pupil and into, and through the lens must be preserved. To some extent backscatter measurements will delineate changes in intensity of light that passes through the lens and also the changes in the direction of the light ray in passing through the lens. They will not, however, identify changes in the wavelength of the light that enters the lens and excites the lens to photoluminescence. Thus backscatter measurements fall short of a complete delineation of the optical properties of the lens that determine the retinal image in the immediate area of the visual axis, hence that determine visual function.

Moreover, because a cataract is a special species of opacity, by focusing on the measurement of any opacity, backscattering studies themselves may give little information about the cataractogenic process. Only a method that is sensitive to the opacity precursor, and which characterizes the light that directly reaches the macula that immediately surrounds the point of intersection with the visual axis 13 of the eye, after passing through the part of the lens that is most responsible for the macula image, can provide information about cataractogenesis as defined by Harding. Thus, the backscattering measurements are not an optimal indicator of the visual severity of a cataract, possibly indicating a greater or lesser visual impairment than that actually suffered by a patient.

Visual acuity tests, which employ high contrast targets, also fall short of completely characterizing visual dysfunctions suffered by a patient with a cataract. For example, visual acuity under one set of lighting conditions may be minimally impaired by a cataract, yet totally impaired in the presence of a glare source, e.g., the headlights of an oncoming automobile at night. As another example, a patient with a cataract may be able to recognize a high contrast target, but be unable to distinguish low contrast features such as a face of another person a few feet away. Other visual dysfunctions experienced by patients with cataracts include bothersome dimness of vision, loss of color discrimination for the short wavelength end of the spectrum, and clouded and indistinct vision. The onset of these dysfunctions may be so gradual that their presence is recognized only after the cataractous lens is removed and replaced with a lens that restores visual function. The latter visual dysfunctions are rarely detected by visual acuity tests that use high contrast letters or figures, nor are they readily identified by backscatter measurements.

The present invention takes a different approach to cataract determination by assessing a throughput quality of a human crystalline lens as it affects color perception of a patient. Optical factors affecting the patient's color perception and color matching behavior include absorption, scattering of light as it passes through the lens of the cataractous-eye and photoluminescence from the lens as it impinges upon the retina. In the present invention, the throughput characteristics of a lens are inferred from a patient's color mixing behavior in accordance with how much a given color mixture as provided by the patient differs from an age matched standard color mixture. The rationale for this inference rests upon the presumption that the throughput characteristics of a lens are wavelength dependent, which wavelength dependency affects the patient's perception of given color mixtures. In addition, it is presumed that the wavelength dependency of a lens is affected by a cataract and its precursor conditions. Therefore, by determining the wavelength dependent characteristics of the lens, an assessment can be made of the presence, and/or stage of development, of a cataract or its precursor conditions.

Before the specifics of the present invention are described, some background information regarding colorimetry as pertaining to this invention will be useful. Colorimetry is based upon many observations of human additive color mixtures, the second described below, is especially relevant to this invention. The first observation is that two separate lights of identical spectral make-up, whether of broad or narrow band, and of the same luminance, will, other things being equal, appear identical to an observer. The second observation is that different additive mixtures, wherein each separate mixture consists of two or more specifically selected lights of differing spectral composition, can be individually adjusted in brightness such that the mixed lights appear indistinguishable, i.e., exactly matched to the same observer. To those skilled in the art, the lights of the first observation are known as non-metameric, whereas the lights of the second observation are known as metameric. These two observations taken together establish the corollary that the perceived color of light is not solely governed by its wavelength composition, and that human color perception is non-analytic in the sense that it can not resolve a perceived color into its identifiable components (or Newton would not be remembered as the first to show that sunlight can be decomposed into a multi-hued spectrum).

It is emphasized that the appearance of a given chromatic or achromatic light is subjective. At present, no means for objective observation of color perceptions is known. Nevertheless, additive mixtures of lights that give rise to metameric colors have been the focus of work by such historical figures as Newton, Helmholtz, Maxwell, Grassman and Schroedinger. This work has been formalized in a graph known as the "CIE Chromaticity Diagram," as reproduced in FIG. 2. See Judd and Wyszecki, *Color and Business, Science and Technology*, 3rd Ed., New York, 1975, and Wright, *The Measurement of Colour*, 4th Ed., New York 1969.

Figure 2:
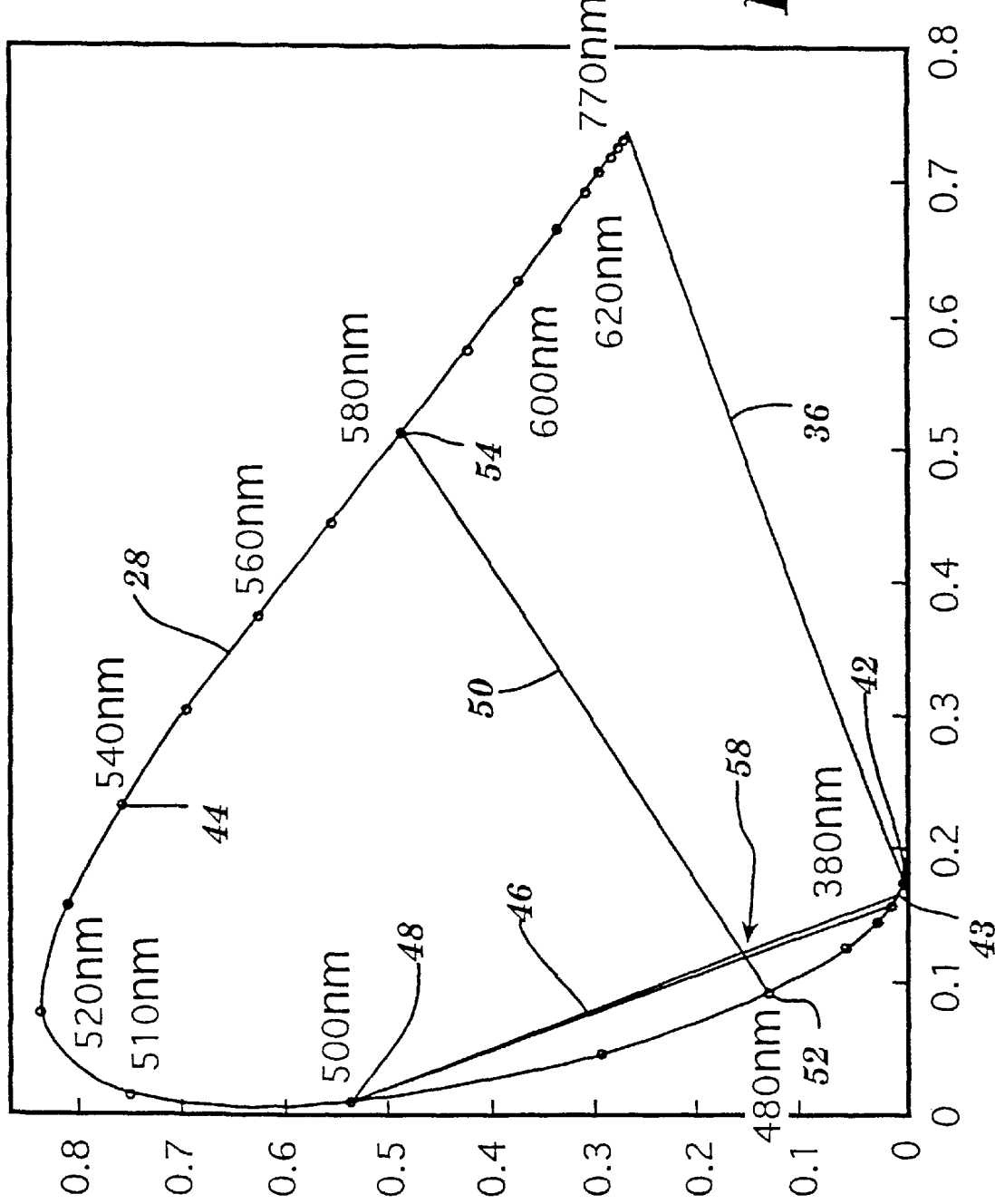
FIG. 2 is a two degree (2°) chromaticity diagram (after CIE) with particular chords thereon.

With reference to FIG. 2, the area confined within the inverted 'U'-shaped curve, 28, portrays all realizable colors obtainable by mixing single spectral wavelengths or very narrow bands of spectral lights. Curve 28 represents the coordinate positions of spectral lights, the so-called "spectrum locus" of colorimetry on the chromaticity graph. Those skilled in the art of colorimetry know that curve 28 is derived from, summarizes, and is referable to the results of metameric color matches made by observers with normal color vision, i.e., normal trichromats. In making such mixtures these observers employed three selected physical lights (e.g., a red, a green, and a blue light) to match all spectral and extra-spectral lights (the purples). It is Grassmann's Laws of Color Mixing that enable the creation of transformed imaginary primaries that form the bases of the CIE diagram. However, it is a long established axiom that a minimum of three additively mixable lights is required to match every spectral and extra-spectral (region 36) color. Generally, these primaries are selected so that two (e.g., a red and a blue light) come from opposing ends of the spectrum and the third (e.g. a green light) comes from the mid-region of the spectrum. The CIE Chromaticity Diagram illustrates for a given chromaticity, i.e., hue and saturation, a relative level for two of the primaries along the x and y axes. When the graph represents an equal luminance plane, the magnitude of the third primary component (represented by a third perpendicularly related z axis not shown) can be derived from the levels (transformed) of the x and y imaginary primary components. The graph is normalized wherein the algebraic sum of x, y and z is equal to 1.0. Thus, the various points within the curve may be specified with reference to two of the primaries (i.e., x and y) alone wherein the third primary is derived according to the relationship of x+y+z=1. Note that an equal energy white (for the "standard observer") on the chromaticity diagram has the coordinates of x=0.33, y=0.33 and accordingly z=0.33. As used herein "real lights" or physical primaries, as contrasted to "imaginary lights" generally refer to lights most proximate the spectrum locus or to mixtures represented as very near the spectrum locus. "Imaginary lights" or imaginary primaries refer to lights that are beyond the spectrum and the extra spectral loci.

Throughout much of the visible spectrum, i.e., from about 380 nm (point 42 on curve 28) to about 540 nm (point 44 on curve 28), mixtures of two of these primary spectral lights, one from the short wavelength region (a "blue") and one from the mid wavelength region (a "green"), will substantially match the color of a spectrum light lying on curve 28 between points 42 and 44. The match will only be approximate, however, because its resulting mixture will appear desaturated relative to the spectrally purer light on the spectrum locus that the mixture is attempting to match.

The term desaturated refers to the appearance of a spectral light of a first wavelength to which has been additively mixed one or more spectral lights of other wavelengths, well removed in the spectrum from the first wavelength light. Such additions render the mixture desaturated. A spectral light, represented as lying on curve 28, is by definition 100% saturated. Thus, to obtain an exact match of a light mixture of two spectrally removed lights (e.g., from the 380–540 nm region of curve 28) to a spectral light therebetween, it is necessary to desaturate the spectral light by the addition to it of at least a third light from the 540–700 nm region of curve 28. Effectively this adds a "negative" amount of light to the mixture of the two spectrally removed lights within the 380–540 nm region, making the intermediate spectral light less saturated and bringing the two mixtures to an exact match within the area bounded by the spectral and extraspectral loci. (While it is most efficient to use the complementary wavelength to the intermediate spectral light for this purpose, mixtures of other lights will serve as well, provided they do not lie between the two from the 380–540 nm part of the spectrum.)

If a straight line 46 is drawn from point 43 on curve 28 (about 407 nm) to point 48 on curve 28 (about 500 nm), line 46 will represent the locus of all mixtures of spectral lights of 407 nm and 500 nm. If a light mixture on line 46 is predominantly of 407 nm wavelength light, then we can infer that the mixture will be perceived as similar to the blue or violet region of the spectrum (by a color normal observer). On the other hand, should the light mixture contain predominantly 500 nm wavelength light, it can be expected to appear greener to the same observer. Note that line 46 drawn between the 407 nm point 43 of curve 28 and the 500 nm point 48 of curve 28 does not pass through the equal energy spectrum region, represented at coordinates x=0.33 and y=0.33; therefore, whatever the ratio of luminance of 407 nm light and 500 nm light, light mixtures along line 46 can always be expected to appear chromatic, i.e., to have an identifiable color when viewed by any color normal observer.

Line 50 is drawn from point 52 on curve 28 (about 480 nm) to point 54 on curve 28 (about 580 nm), and represents all mixture ratios possible from mixtures of these two lights. If the mixture contains more light of wavelength 480 nm relative to 580 nm wavelength light, it will appear bluer to a color normal observer, whereas it will appear yellower if it contains more 580 nm light relative to the 480 nm light. At some ratio of the 480 nm light and the 580 nm light, the mixture can be represented by a point along line 50 proximate the coordinates (0.33, 0.33). It will then appear achromatic. Any pair of spectral lights providing a light mixture having such an achromatic quality is said to be a complementary pair.

There are three corollaries to the above additive color mixing rules pertinent to this invention. The first corollary is that any point not on curve 28, but within its confines, represents a light mixture comprising two or more real spectral lights. The second corollary is that any point within the confines of curve 28 can be represented by, and will be exactly matched in hue, saturation and brightness, by a number of different combinations of real spectral lights, provided that any such combination is adjusted to provide a mixture of the same luminance as the mixture to which it is compared. For example, in FIG. 2, point 58 can be represented by a mixture of, among others, 480 nm and 580 nm wavelength light, or a mixture of 407 nm and 500 nm wavelength light. The third corollary is that if exactly matched, the sum of the luminances of the components of each of the two metameric mixtures are equal to each other. In other words, the total luminance of the components of each of the composite lights of one pair will be equal to that of the other pair.

It should be noted that the CIE system applies to normal trichromats without regard to their age, to their eye color, to their complexion (skin color), or to their gender. It also applies to all real lights of the visible spectrum and their mixtures.

A method according to one aspect of the present invention will now be described with reference to testing an eye of a patient for a cataract or for the relative concentration of a cataract precursor. First, the patient establishes monocularly, for the eye to be tested, an exact match between separate pairs of spectral lights in a two degree (2°) photometer field delivering all lights at a photopic level. Photopic level refers to a luminous level of a spectral light that is above the color threshold, and is generally considered to be of daylight intensity. For the purposes of the present invention, an exact match is one in which all parts of the photometer field appear identical in hue, saturation and brightness to the patient.

Although various spectral pairs of lights may be used for the patient to establish a match, a first pair preferably comprises 407 nm (actually 410 nm in one embodiment) wavelength light selected to maximally excite the fluorophore of the human lens whose photoluminescent spectra peaks in the 490–530 nm range and a 500 nm wavelength light (hereinafter Pair I). A second pair (hereinafter Pair II) comprises 480 nm wavelength (standard wavelength I) light and 580 nm wavelength (standard wavelength II) light. As will be described more fully subsequently, these particular wavelength lights may be provided by white light that is filtered by interference filters, or alternatively monochromators, with about 10 to 15 nm Full Width Half Maximum (FWHM) bandwidths. The filtering provided by an interference filter can be tuned by pivoting the filter slightly with respect to the longitudinal optical propagation axis of light passing there through. This angular adjustment provides a translation of the filter's associated peak spectral response from a normal wavelength to a new wavelength shifted by as much as several nanometers. Although lights of such origins do not lie precisely on the spectrum locus, their departures therefrom do not significantly affect the operation of this invention. An exact match between the first and second pairs is possible for a color normal observer since the respective chords of the two separate pairs intersect within the confines of curve 28. It will be understood that, in practice, light of exactly a given wavelength may not be possible with currently available equipment; thus, some degree of wavelength flexibility is presumed. Such flexibility in designated wavelengths will be deemed not to significantly impair the diagnostic capability of this instrument. However, the 'violet' of Pair I should be about 407 nm, the 'green' of Pair I should be about 500 nm, and the 'blue' of pair II should be about 480 nm with the 'yellow' of Pair II, its complement, about 580 nm in this embodiment.

Anyone asked to produce an exact color match with any type of calorimeter must be conversant with the vocabulary of color science or made so by instruction. Some persons will readily understand the requirement that they are to adjust the instrument so that all parts of the photometer field appear uniform in color throughout. Others, however, will need more specific instruction for which the following will serve.

Seven approximately 2 inch discs, which have been coated with opaque paints, comprise the instructional materials for a given user. Disc 1, 2 and 3 are painted with a "sky" blue paint. Disc 4 is painted with an even mixture of the above blue plus about 25% of a similar white paint. Disc 5 is painted with an even mixture of the above blue plus 3% of a black paint. Disc 6 is painted with a green of approximately equal brightness to the blue of disc 1, 2 and 3. Disc 7 consists of an even mixture of 90% blue and 10% of the above green. Six of the 2 inch discs, namely, 2, 3, 4, 5, 6 and 7 are then bisected into hemi-discs.

Before beginning the instrumental test, the patient is presented with the six pairs of hemi-discs, numbers 2–7, that have been randomly arranged on a neutral gray surface (out of sight of the patient). When these are brought into view, the patient is requested to look at the hemi-discs and to select the one, or ones, that match one of the halves of disc number 2 so that the joined hemi-discs look like the uncut disc number 1. If the patient selects the hemi-discs cut from number 3 or the other half of number 2, and only these, then it may be concluded that the request to establish an exact match in the calorimeter is understood. If not, then more replication, testing and instruction is required. It is further understood that if these same set of discs are to be reused, that they must not be soiled by handling. All discs must be replaced if wear and tear cause differential discoloration of disc 1 and the hemi-discs of disc 2 and 3.

Once it is established that the patient understands what a color match comprises, the patient is provided in a first half of a two degree (2°) photometer field, a light mixture comprising the components of Pair I, and in a second half of the photometer field 480 nm wavelength light alone (standard wavelength I). The patient is then requested to adjust the power ratio of the components in the Pair I mixture so as to match, in hue, the 480 nm wavelength light.

Once this is done, 580 nm wavelength light (standard wavelength II), referred to as the desaturant, is added to the 480 nm light (providing a Pair II mixture) until the patient perceives that the two halves of the photometer field match closely in both hue and saturation. Once the mixtures associated with the two halves of the photometer field have been matched closely, the patient is then permitted minimal adjustment of all four lights in order to establish an exact match between the mixtures of the respective photometer fields. In practice, it has been observed that most patients describe the color of these particular pairs, when matched, as resembling the clear northern sky. For a color normal observer, the match of the two separate mixtures would be representative of point 58, in FIG. 2, where line 46 intersects line 50.

In greater particularity, the instrument presents four controls for patient manipulation. For a patient not skilled in the art of colorimetry, a request to produce an exact match between the two parts of a photometer field could take a considerable length of time, even if the concept of an exact match is understood. Therefore, in order to assist the patient during the manipulative part of the task, the 480 nm wavelength light (standard wavelength I) component of Pair II is set to some supra photoptic power level to serve as a reference, and the 407 nm wavelength light and 500 nm wavelength light of the Pair I light mixture are then altered in a reciprocal fashion to one another so as to maintain a constant luminance for the resulting mixture approximately equal to that of the 480 nm wavelength light reference (standard wavelength I). Neutral density wedges for attenuating the respective lights are brought under the control of a microprocessor so that the patient can set the 407–500 nm light mixture (Pair I) to match the hue of 480 nm wavelength light as closely as possible by a converging staircase or ramp procedure (up and down psychophysical method) via the microprocessor.

The application of a microprocessor to control a converging (up and down) staircase or ramp procedure is described by Ostrander et al; "A Preferential Looking Clinical Acuity Test: Improvement in Implemented Microcomputer Control", Behavior Research Methods, Instruments, & Computers; 21 (4); 1989; pp. 421–425; hereby incorporated by reference. The microprocessor assisted procedure provides a differential response between the two lights of the first mixture. If the mixture is too blue or violet, the patient responds by signaling the microprocessor to provide more of the green primary light. The microprocessor then adjusts the attenuation settings for the 407 nm wavelength light and the 500 nm wavelength light so that the 500 nm component is increased and the 407 nm component decreased while preserving the total luminance of the mixture. Conversely, if the mixture is too green, the patient signals the microprocessor to provide more blue.

Once a provisional match (in hue) to the 480 nm wavelength reference light is achieved, the patient signals the microprocessor to add 580 nm wavelength light (standard wavelength II), the desaturant, to the 480 nm wavelength light (standard wavelength I). A new differential response is provided by the microprocessor so that if the 480–580 nm light mixture, Pair II mixture, is too saturated, the patient signals the microprocessor to provide more 580 nm wavelength light (standard wavelength II), and if the mixture is too desaturated, the patient signals the microprocessor to supply less 580 nm wavelength light. Preferably, for each of the Pair I and Pair II mixtures, reciprocal adjustment of associated component neutral density attenuators is provided by the microprocessor so that each resulting mixture has a constant luminance as the mixture ratios are changed. The attenuators should provide incremental adjustments of less than 4% and preferably are continuously adjustable attenuators. After this provisional adjustment for the Pair II mixture, the patient is then allowed independent minimal adjustment of all four light components in order to obtain an exact match between the Pair I mixture and the Pair II mixture.

It should be noted that point 58, with reference to FIG. 2, at the intersection of lines 46 and 50, is not a color nor does it represent a geometric point. It merely represents the luminance ratios of the light components of the Pair I and Pair II mixtures that, to a color normal observer, cause the two respective mixtures to appear indistinguishable in hue, saturation and brightness. In actuality, a finite area surrounds the intersection of chords 46 and 50 within which a patient is unable to distinguish between the two separate mixtures.

After the patient has reported an exact match, between the Pair I and Pair II mixtures, the light components of the Pair I mixture and 480 nm wavelength light (standard wavelength I) of the Pair II mixture are fixed at their corresponding levels that provided the match as set by the patient. The luminance of the 580 nm wavelength light component (standard wavelength II) of the Pair II mixture is then adjusted to a luminance different from the previous match point. The patient is then requested to reestablish an exact match of the Pair II mixture to the Pair I mixture by varying only the luminance of the 580 nm wavelength light component (standard wavelength II) relative to the fixed luminance of the 480 nm wavelength light component. This sequence of offset and rematch is repeated a number of times, preferably 10 or so, in order to further establish that the patient understood the matching task and is able to provide a consistent match. The luminance of the 580 nm wavelength component (standard wavelength II) is determined and recorded for each rematch. The mean and standard deviation for the luminance level of the 580 nm wavelength light from the above matching procedure are then computed. A standard deviation of more than about 4% of the mean value indicates that either the matching task was not well understood by the patient, or that the patient may have some form of ocular defect for which the present invention is not a suitable diagnostic method. When the standard deviation is outside the 4% range, the entire protocol is reperformed to rule out the possibility that the patient has merely misunderstood the matching instructions. If the standard deviation is within 4% of the mean value, then the procedure continues wherein the 580 nm wavelength light is adjusted to the mean luminance level. Note that in the preferred embodiment, the threshold for the standard deviation is set to 4% of the mean value; however, the percentage used may change depending upon the instrument characteristics but should be well under 10% of the mean luminance value.

Assuming the standard deviation to be within the narrow range selected, the 407 nm wavelength light component of the Pair I mixture is replaced by a 440 nm wavelength light. The luminance levels of the other lights, the Pair II lights and the 500 nm wavelength light component of Pair I, remain fixed at the Pair I–Pair II matched levels. The mixture of the 440 nm wavelength light and 500 nm wavelength light will hereinafter be referred to as "Pair III". The luminance of the 440 nm wavelength light is then adjusted so as to bring the two halves of the photometer field, the Pair II and Pair III mixtures, to a matching condition, as perceived by the patient. Again, it is understood that point 58 in FIG. 2 is not, strictly speaking, an exact point, but rather a small area in color space within which an observer is unable to distinguish between different light mixtures. For practical purposes, any mixtures falling within such an area are considered to be exactly matched. Once the Pair III mixture is matched to the Pair II mixture, the luminance level of the 440 nm wavelength light is determined. Note that any luminance determinations are based upon power level measurements of a radiometer in watts, divided by an associated area and then compensated by an associated luminosity coefficient established in accordance with the wavelength of the light measured.

By assuming a normalized illuminated area of one for the area of the photometer field illuminated by a given wavelength light component, the luminance value of each wavelength light component is determined by multiplying the power level of the component by a luminosity co-efficient associated with the component's wavelength as shown here below in equation 1:

$$L_\lambda = V_\lambda \times P_\lambda \qquad \text{Eq. 1}$$

$L_\lambda$=Luminance at wavelength $\lambda$,
$V_\lambda$=Luminosity coefficient at wavelength $\lambda$,
$P_\lambda$=Power level of light at wavelength $\lambda$, Luminosity coefficients are obtained from an available table referencing the luminous efficiency of the eye with respect to the light's wavelength. See A.S.T.M. E-308, "Standard Practice for Computing the Colors of Objects by Using the CIE System, $\overline{Y}_\lambda = V_\lambda$ exactly, Table-1, as provided here below.

| $\lambda V_M (\lambda)$ | $\lambda V_M (\lambda)$ | $\lambda V_M (\lambda)$ |
|---|---|---|
| 380 0.20000E-03 | 415 0.11779E-01 | 450 0.46800E-01 |
| 381 0.22821E-03 | 416 0.12842E-01 | 451 0.47743E-01 |
| 382 0.26109E-03 | 417 0.13956E-01 | 452 0.48733E-01 |
| 383 0.29936E-03 | 418 0.15111E-01 | 453 0.49785E-01 |
| 384 0.34387E-03 | 419 0.16297E-01 | 454 0.50910E-01 |
| 385 0.39556E-03 | 420 0.17500E-01 | 455 0.52122E-01 |
| 386 0.45544E-03 | 421 0.18582E-01 | 456 0.53435E-01 |
| 387 0.52462E-03 | 422 0.19645E-01 | 457 0.54864E-01 |
| 388 0.60428E-03 | 423 0.20883E-01 | 458 0.56424E-01 |
| 389 0.69565E-03 | 424 0.21694E-01 | 459 0.58131E-01 |

-continued

| λV_M (λ) | λV_M (λ) | λV_M (λ) |
|---|---|---|
| 3900.80000E-03 | 4250.22678E-01 | 4600.60000E-01 |
| 3910.91635E-03 | 4260.23636E-01 | 4610.62601E-01 |
| 3920.10477E-02 | 4270.24572E-01 | 4620.65277E-01 |
| 3930.11955E-02 | 4280.25490E-01 | 4630.68042E-01 |
| 3940.13611E-02 | 4290.26397E-01 | 4640.709110-01 |
| 3950.15457E-02 | 4300.27300E-01 | 4650.73900E-01 |
| 3960.17508E-02 | 4310.28335E-01 | 4660.77016E-01 |
| 3970.18776E-02 | 4320.29383E-01 | 4670.80266E-01 |
| 3980.22273E-02 | 4330.30442E-01 | 4680.83666E-01 |
| 3990.25011E-02 | 4340.31510E-01 | 4690.87232E-01 |
| 4000.28000E-02 | 4350.32584E-01 | 4700.90980E-01 |
| 4010.31159E-02 | 4360.33681E-01 | 4710.94917E-01 |
| 4020.34576E-02 | 4370.34735E-01 | 4720.99045E-01 |
| 4030.38268E-02 | 4380.35803E-01 | 4730.10387E 00 |
| 4040.42256E-02 | 4390.36860E-01 | 4740.107884 00 |
| 4050.46562E-02 | 4400.37900E-01 | 4750.11260E 00 |
| 4060.51216E-02 | 4410.38838E-01 | 4760.11753E 00 |
| 4070.56248E-02 | 4420.39675E-01 | 4770.12267E 00 |
| 4080.61695E-02 | 4430.40646E-01 | 4780.12799E 00 |
| 4090.67597E-02 | 4440.41524E-01 | 4790.13345E 00 |
| 4100.74000E-02 | 4450.42391E-01 | 4800.13902E 00 |
| 4110.81451E-02 | 4460.43252E-01 | 4810.14467E 00 |
| 4120.89555E-02 | 4470.44116E-01 | 4820.15046E 00 |
| 4130.98322E-02 | 4480.44990E-01 | 4830.15646E 00 |
| 4140.10774E-01 | 4490.45881E-01 | 4840.16271E 00 |
| 4850.16930E 00 | 5250.79320E 00 | 5650.97860E 00 |
| 4860.17624E 00 | 5260.80811E 00 | 5660.97408E 00 |
| 4870.18355E 00 | 5270.82249E 00 | 5670.96917E 00 |
| 4880.19127E 00 | 5280.83630E 00 | 5680.96385E 00 |
| 4890.19941E 00 | 5290.84949E 00 | 5690.95813E 00 |
| 4900.20802E 00 | 5300.86200E 00 | 5700.95200E 00 |
| 4910.21719E 00 | 5310.87381E 00 | 5710.94545E 00 |
| 4920.22673E 00 | 5320.88496E 00 | 5720.93849E 00 |
| 4930.23685E 00 | 5330.89549E 00 | 5730.93116E 00 |
| 4940.24748E 00 | 5340.90544E 00 | 5740.92345E 00 |
| 4950.25860E 00 | 5350.91485E 00 | 5750.91540E 00 |
| 4960.27018E 00 | 5360.92373E 00 | 5760.90700E 00 |
| 4970.28229E 00 | 5370.93209E 00 | 5770.89827E 00 |
| 4980.29505E 00 | 5380.93992E 00 | 5780.88920E 00 |
| 4990.30857E 00 | 5390.94722E 00 | 5790.87978E 00 |
| 5000.32300E 00 | 5400.95400E 00 | 5800.87000E 00 |
| 5010.33840E 00 | 5410.96025E 00 | 5810.85986E 00 |
| 5020.35468E 00 | 5420.96600E 00 | 5820.84939E 00 |
| 5030.37169E 00 | 5430.97126E 00 | 5830.83862E 00 |
| 5040.38928E 00 | 5440.97602E 00 | 5840.82758E 00 |
| 5050.40730E 00 | 5450.98030E 00 | 5850.81630E 00 |
| 5060.42552E 00 | 5460.98409E 00 | 5860.80479E 00 |
| 5070.44430E 00 | 5470.98748E 00 | 5870.79308E 00 |
| 5080.46339E 00 | 5480.99031E 00 | 5880.78119E 00 |
| 5090.48293E 00 | 5490.99281E 00 | 5890.76915E 00 |
| 5100.50300E 00 | 5500.99495E 00 | 5900.75700E 00 |
| 5110.52356E 00 | 5510.99671E 00 | 5910.74475E 00 |
| 5120.54451E 00 | 5520.99809E 00 | 5920.73242E 00 |
| 5130.56569E 00 | 5530.99911E 00 | 5930.72000E 00 |
| 5140.58696E 00 | 5540.99974E 00 | 5940.70749E 00 |
| 5150.60820E 00 | 5550.10000E 00 | 5950.69490E 00 |
| 5160.62934E 00 | 5560.99885E 00 | 5960.68221E 00 |
| 5170.65030E 00 | 5570.99930E 00 | 5970.66947E 00 |
| 5180.67087E 00 | 5580.99832E 00 | 5980.65674E 00 |
| 5190.69084E 00 | 5590.99689E 00 | 5990.64384E 00 |
| 5200.71000E 00 | 5600.99500E 00 | 6000.63100E 00 |
| 5210.72818E 00 | 5610.99260E 00 | 6010.61815E 00 |
| 5220.74546E 00 | 5620.98974E 00 | 6020.60531E 00 |
| 5230.76196E 00 | 5630.98644E 00 | 6030.59247E 00 |
| 5240.77783E 00 | 5640.98272E 00 | 6040.57963E 00 |
| 6050.56680E 00 | 6450.13820E 00 | 6850.11920E-01 |
| 6060.55396E 00 | 6460.13150E 00 | 6860.11068E-01 |
| 6070.54113E 00 | 6470.12502E 00 | 6870.10273E-01 |
| 6080.52835E 00 | 6480.11877E 00 | 6880.95333E-02 |
| 6090.51563E 00 | 6490.11276E 00 | 6890.88461E-02 |
| 6100.50300E 00 | 6500.10700E 00 | 6900.82100E-02 |
| 6110.49046E 00 | 6510.10147E 00 | 6910.76237E-02 |
| 6120.47803E 00 | 6520.96218E-01 | 6920.70854E-02 |
| 6130.46567E 00 | 6530.91122E-01 | 6930.65914E-02 |
| 6140.45340E 00 | 6540.86264E-01 | 6940.61384E-02 |
| 6150.44120E 00 | 6550.81600E-01 | 6950.57230E-02 |
| 6160.42908E 00 | 6560.77120E-01 | 6960.53430E-02 |
| 6170.41703E 00 | 6570.72825E-01 | 6970.49957E-02 |
| 6180.40503E 00 | 6580.68710E-01 | 6980.46764E-02 |
| 6190.39303E 00 | 6590.64769E-01 | 6990.43800E-02 |
| 6200.38100E 00 | 6600.61000E-01 | 7000.41020E-02 |
| 6210.36891E 00 | 6610.57396E-01 | 7010.38384E-02 |
| 6220.35682E 00 | 6620.53955E-01 | 7020.35890E-02 |
| 6230.34477E 00 | 6630.50673E-01 | 7030.33542E-02 |
| 6240.33281E 00 | 6640.47549E-01 | 7040.31340E-02 |
| 6250.32000E 00 | 6650.44580E-01 | 7050.29290E-02 |
| 6260.30933E 00 | 6660.41758E-01 | 7060.27381E-02 |
| 6270.29785E 00 | 6670.39084E-01 | 7070.25598E-02 |
| 6280.28659E 00 | 6680.36583E-01 | 7080.23924E-02 |
| 6290.27562E 00 | 6690.34200E-01 | 7090.22372E-02 |
| 6300.26500E 00 | 6700.32000E-01 | 7100.20910E-02 |
| 6310.25476E 00 | 6710.29962E-01 | 7110.19535E-02 |
| 6320.24488E 00 | 6720.28076E-01 | 7120.18245E-02 |
| 6330.23533E 00 | 6730.26329E-01 | 7130.17035E-02 |
| 6340.22605E 00 | 6740.24708E-01 | 7140.15901E-02 |
| 6350.21700E 00 | 6750.23200E-01 | 7150.14840E-02 |
| 6360.20816E 00 | 6760.21800E-01 | 7160.13844E-02 |
| 6370.19954E 00 | 6770.20501E-01 | 7170.12912E-02 |
| 6380.19115E 00 | 6780.19281E-01 | 7180.12040E-02 |
| 6390.18297E 00 | 6790.18120E-01 | 7190.11227E-02 |
| 6400.17500E 00 | 6800.17000E-01 | 7200.10470E-02 |
| 6410.16722E 00 | 6810.15903E-01 | 7210.97658E-03 |
| 6420.15964E 00 | 6820.14837E-01 | 7220.91110E-03 |
| 6430.15227E 00 | 6830.13810E-01 | 7230.85013E-03 |
| 6440.14512E 00 | 6840.12834E-01 | 7240.79323E-03 |

For the Pair I and Pair III lights, the following proportions are calculated:

$$\text{Pair I} \quad \frac{L_{500}}{L_{407} + L_{500}}; \text{ and} \qquad \text{Eq. 2}$$

$$\text{Pair III} \quad \frac{L_{500}}{L_{440} + L_{500}}, \qquad \text{Eq. 3}$$

where $L_{500}$ is the compensated luminance for the incident 500 nm wavelength light component of the Pair I and Pair III mixtures respectively; $L_{407}$ is the compensated luminance for the incident 407 nm wavelength light component of the Pair I mixture; and $L_{440}$ is the compensated luminance for the incident 440 nm wavelength light component of the Pair III mixture.

It will be apparent to one skilled in the art of colorimetry that the chords drawn in FIG. 2 from the 407 nm point and the 440 nm point on curve 28, each to the 500 nm point, are essentially equal in length. They differ by only 1% and, therefore, the Pair I and Pair III luminance proportion ratios would be expected to be essentially the same for any lens. However, in actuality, these ratios differ from one another in accordance with the stage of cataractogenesis.

Figure 3A:
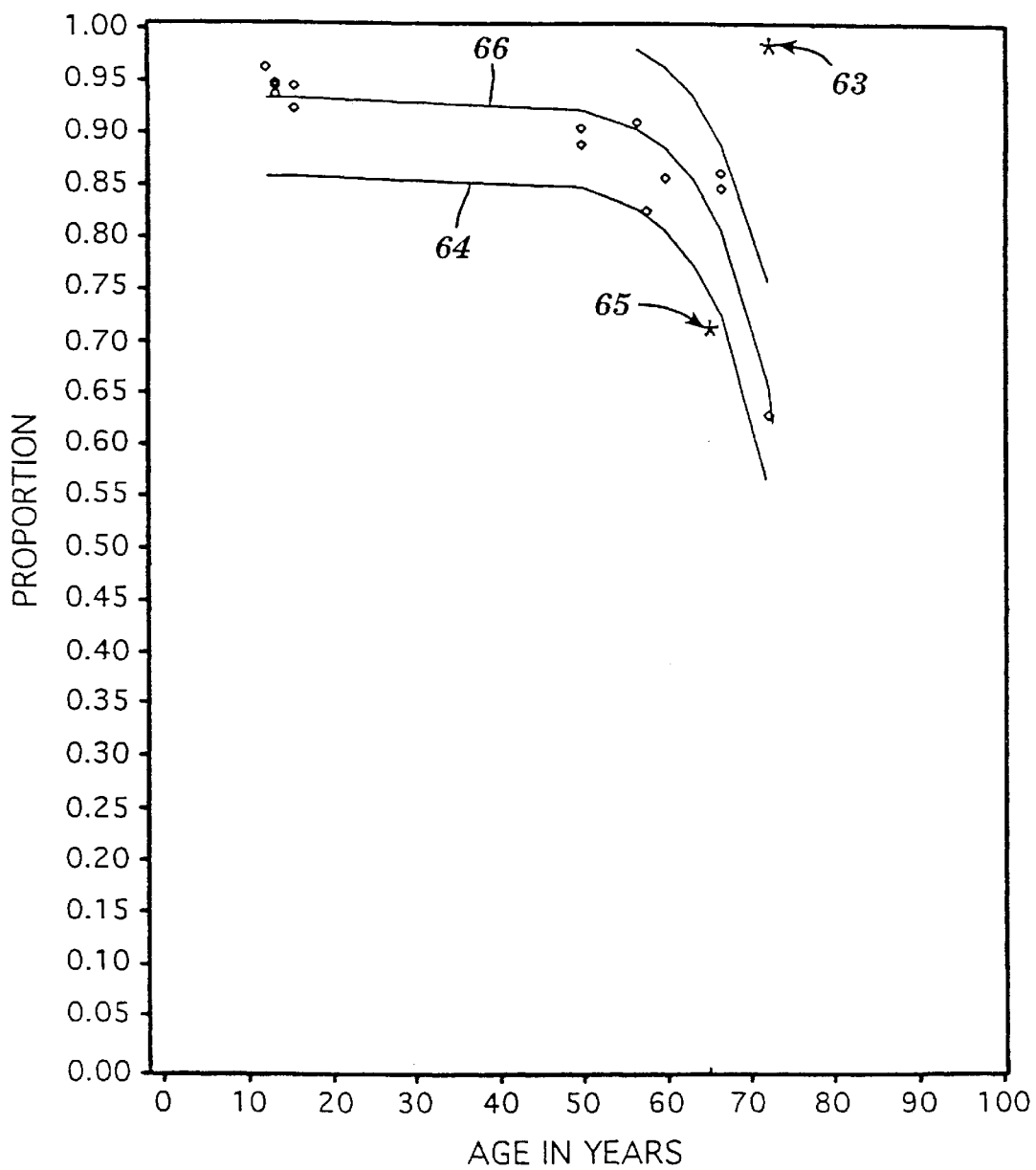
FIG. 3A is a graph showing the effects of age on a primary measurement parameter for inferred lens photoluminescence of a given standardization group.
Figure 4:
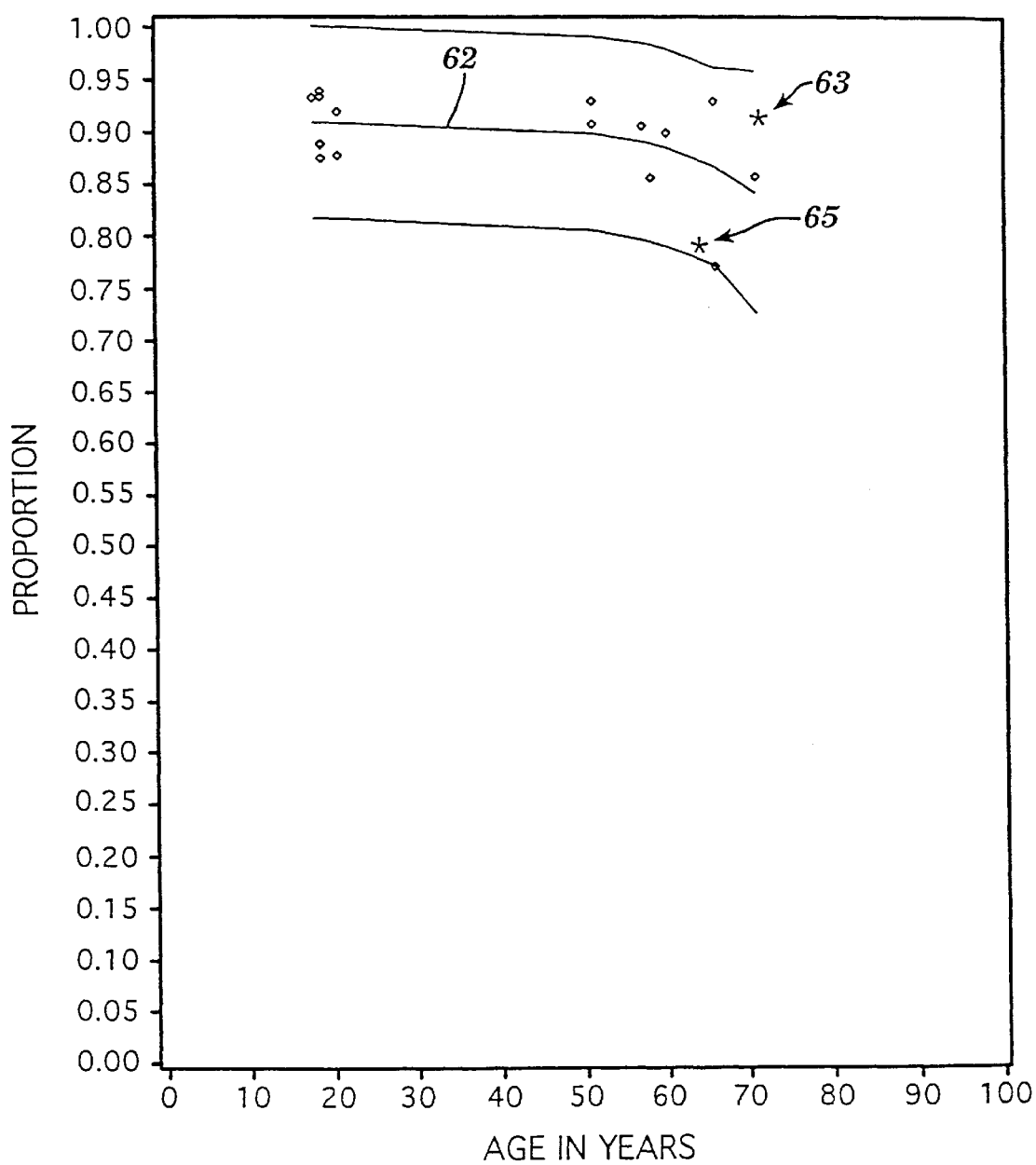
FIG. 4 is a graph similar to FIG. 3A showing the effects of age on a secondary measurement parameter for inferred lens photoluminescence of the given standardization group.

FIGS. 3A and 4 are graphs plotting, with respect to age, Pair I and Pair III luminance proportions respectively for the results of color matches made by 16 European Caucasian American men as a standardization group. They had no visual complaints and wore no corrections when they made the color matches. Preferably separate curves are obtained for standardization groups of particular eye colors and/or complexions for comparison with subjects of similar eye color and/or complexion. The two asterisks 63 and 65 of FIG. 3A represent data points of a 72 year old subject with a PMMA plastic intraocular lens and a 64 year old subject with a surgically mature cataract respectively, which data points are used for comparative purposes only and are not taken as part of the standardization group. It should be noted that the proportions plotted in FIG. 3A were obtained using 410 nm wavelength light in the Pair I mixture instead of a preferred wavelength of 407 nm. The Pair I proportions are plotted in FIG. 3A, and the Pair III proportions are plotted in FIG. 4. Both are plotted with respect to the age of the subject.

Curve 66 is a curve of best fit for the Pair I proportions, and curve 64 is the 95% prediction interval therefor. Standard curve fitting techniques may be employed for fitting a curve to the data points of the standardization group. For example, in one embodiment, curve 66 was obtained per a generalized equation 4 as follows:

$$K_0 + K_1 \exp(K_2 * Age) \qquad \text{Eq. 4}$$

Similarly, curve 62 is a curve of best fit for the Pair III proportions (FIG. 4). The best fit lines 62 and 66 show that each ratio decreases with increasing subject age. It is believed that the departure from an equality prediction for both is due to absorption of the shorter wavelength light by the lens and a proportion thereof being converted by photoluminescence.

Artisans skilled in the arts of measurement theory, scaling theory and psychometric methods will know the techniques for developing a standardization curve for values of a standardization group. After obtaining standardization curves for mixture ratio values of a standardization group, wherein associated luminosity data has been compensated by the above luminosity coefficients, corresponding mixture ratio values taken from a patient under test are compared against the standardization curve and the extent of the differences therebetween are used to determine whether or not a cataract or cataract precursor condition exists within the given patient. These differences are related to the differences between points 63 and 65 in FIGS. 3A and 4. In addition, the proportion values obtained for patients of different ages under test are used to determine the rate of cataractogenesis. The proportions determined are matched to the age equivalent values of the standardization group curves. The slope of the standardization group curve at the value corresponding to that determined for the patient is taken as the stage of cataractogenesis for the patient. Again, it should be noted that the standardization function shown is for a group of European-Caucasian American men. Different standardization functions may be expected from groups of different eye colors or complexions. Different functions may, moreover, be obtained for the women and men of those groups.

Examples of proportion comparisons are shown with reference to FIG. 3A, wherein a Pair I proportion obtained from a 64 year old man with a surgically mature cataract with significant visual acuity impairment, and a Pair I proportion for a 72 year old patient with an intra-ocular PMMA lens, both European-Caucasian men, are plotted with reference to the standardized plots of the standardization group comprising the 16 European-Caucasian American men. The marks of both men, in FIG. 3A, fall beyond their respective 95% prediction interval limits of the standardized data. The Pair I ratio asterisk 63, for the patient with the inter-ocular lens is above the standardized curves 66 and 64 while the Pair I ratio, asterisk 65, for the cataract patient falls below the standardized curves 66 and 64. Thus, the curve for the standardized group (which falls between the marks of the respective sample patients) depicts a rate of development for the concentration of a cataract precursor from the immature concentration level at an early age to the formation of a senile cataract at a later age.

By comparing the ratio values of a test patient to an appropriate standardization curve, the stage of cataract development, the rate of cataractogenesis and cataract onset prediction can be determined in accordance with the placement of the test patient's values relative to the standardization curve. A patient's Pair I ratio value relative the ratio value span between points 63 and 65, i.e. the 72 year old man with the inter-ocular lens and the 64 year old man with cataract respectively in FIG. 3A, indicates the state of cataractogenesis. The slope of the standardization curve at a ratio value corresponding to the ratio value of the test patient provides a rate of cataractogenesis. The number of years along the standardized curve from a first point of a ratio value thereof corresponding to the test patient's ratio value to a second point of a ratio value corresponding to a mature cataract provides a time prediction for an onset of cataracts for the test patient. Finally, the number of years offset between the test patient's ratio value to a point of equivalent value on the standardization curve provides the number of years of accelerated/retarded cataractogenesis.

Figure 3B:
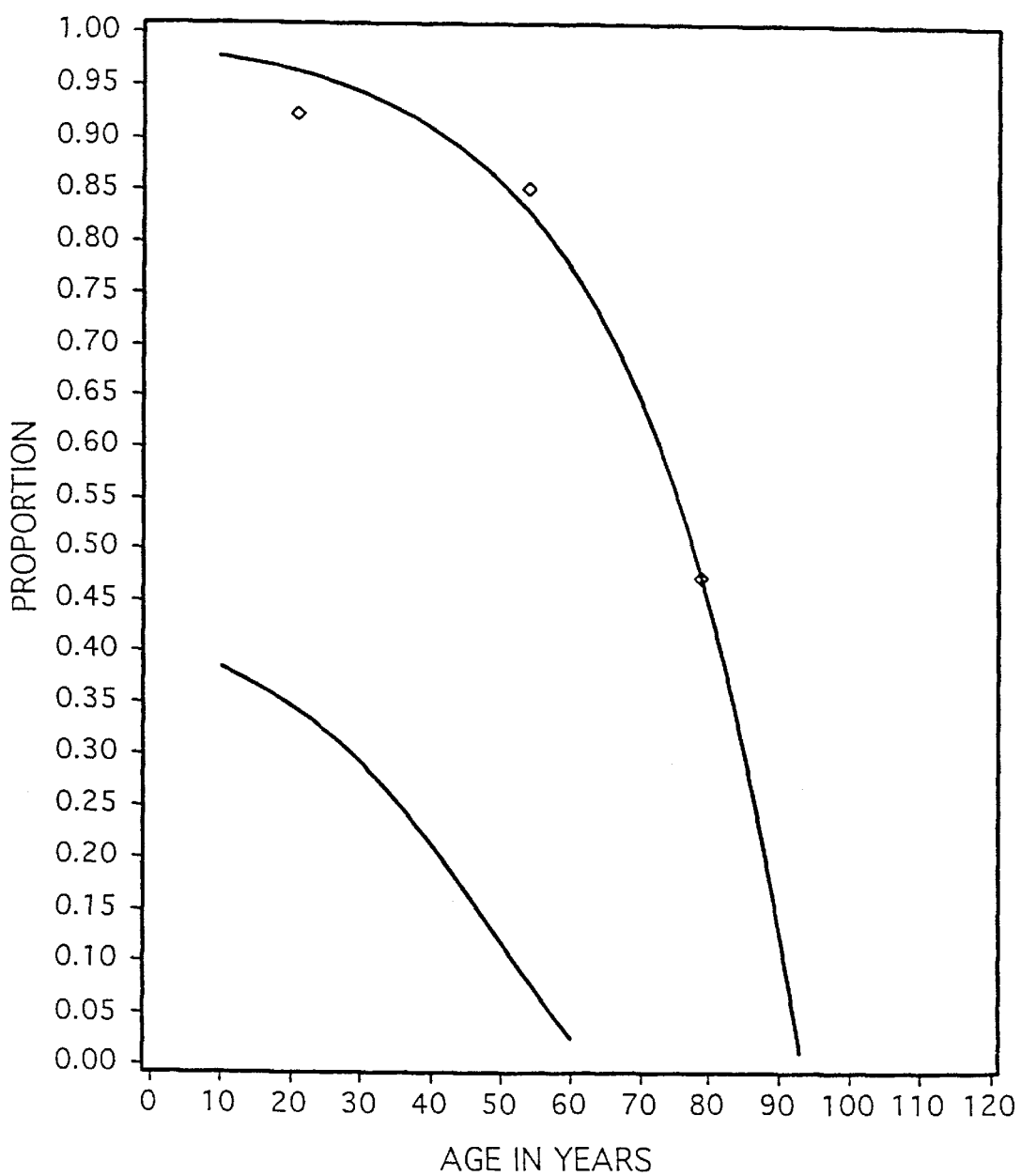
FIG. 3B is a graph showing the accelerated effects relative to non-diabetics of age on the primary measurement parameter for inferred lens photoluminescence for a second (albeit small) standardization group of diabetics.

FIG. 3B shows a standardization curve drawn for a second standardization group of diabetics. A curve was fit to the Pair I ratio values obtained from three diabetic patients. Note that there appears to be an accelerated rate of cataractogenesis in comparison with the associated curves of the standardization group of FIG. 3A.

Thus far, polarization effects have been ignored. However, the full utility of the present invention can be realized, in accordance with a second aspect of the present invention, by considering how color mixture ratios are affected in accordance with polarization of one member of the Pair I mixture. Varying the polarization of light entering the eye from a vertical polarization to a horizontal polarization is believed to cause a change in the forward small particle scattering intensity. Therefore, color matches made with light of different polarizations likewise yield differences in corresponding mixture ratios. This follows from the fact that, in a relative sense, forward scattering is markedly increased in a lens where substantial phase separation has occurred. Such conditions exist in an advanced stage of a maturing cataract. This agrees with observed results wherein older subjects produced greater ratio differences between polarization states than that of younger patients. It has been observed that the polarization affects upon mixture ratios is wavelength dependent. In other words, changing the polarization state of 407 nm wavelength light (excitation light for photoluminescence) changes the Pair I mixture ratio value while changing the polarization state of the 440 nm wavelength light has little influence upon the Pair III ratio value. Accordingly, the method and instrument in accordance with one aspect of the present invention will take into account the polarization of the 407 nm wavelength light component as the patient performs respective color matches.

Figure 7:
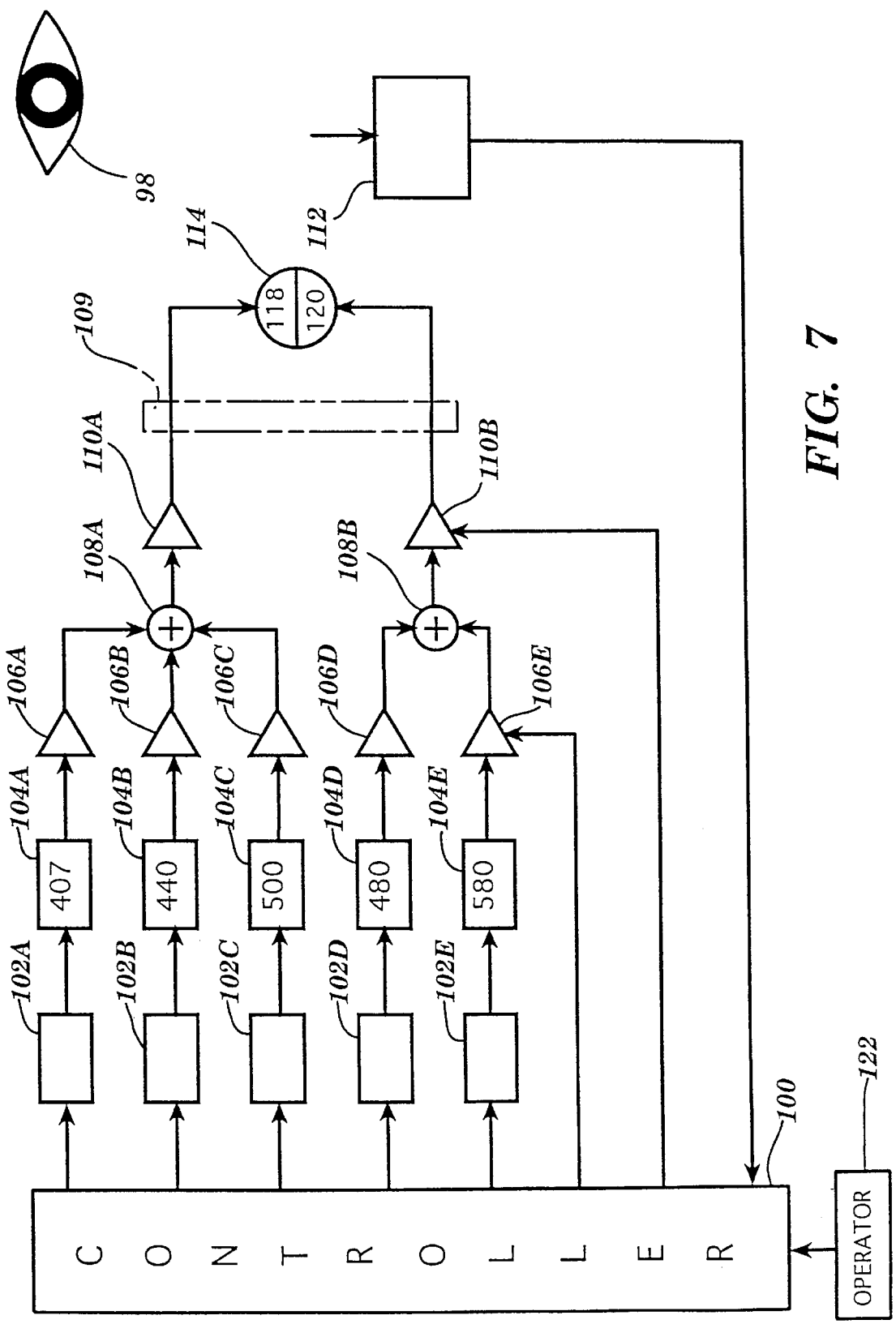
FIG. 7 is a block diagram of an apparatus for assisting the method of the present invention.

With reference to FIG. 7, an apparatus in accordance with the present invention enables a patient to mix light sources for matching light mixtures of given color ratios from which the presence of a cataract or cataract precursor is determined as described hereinbefore. Various light sources 102 are supplied to filters 104 which filter If the light sources to supply desired wavelength light components as necessary for forming mixtures to be incident to photometer field 114. The various wavelength light components as produced are not polarized. Primary attenuators 106 attenuate various filtered light components before the various light components are mixed by mixers 108A and 108B. The light mixtures from mixers 108A and 108B are attenuated by secondary attenuators 110A and 110B before being incident upon respective portions 118, 120 of photometer field 114. Preferably, chopper 109 is interposed in the light paths between mixers 108A,108B and respective portions 118,120 of photometer field 114. The chopper blocks respective light paths in alternating sequence so that photometer field 114 receives the associated light of mixers 108A,108B in alternating sequence. The chopping rate for the chopper is set to be well above the flicker fusion rate. A patient views the respective light mixtures as incident upon photometer field 114 with his/her eye 98 that is being tested. Radiometer 112 measures the power of light as incident upon photometer field 114.

Controller 100, such as a microprocessor, controls various elements of the system in order to supply respective light mixtures upon photometer field 114. The line drawn from controller 100 to attenuator 106E is assumed to represent a plurality of control lines to respective attenuators 106A–106E. Likewise, the line from controller 100 to attenuator 110B represents control lines to both attenuator 110A and attenuator 110B. Assuming a light mixture of 407 nm wavelength light and 500 nm wavelength light are desired to be incident upon a first portion 118 of photometer field 114, then controller 100 will enable light sources 102A and 102C. Light sources 102A and 102C provide incident white light upon respective filters 104A and 104C. Filter 104A filters the white light of light source 102A preferably to output 407 nm wavelength light. Filter 104C on the other hand receives white light from light source 102C and outputs therefrom a spectral light component centered at 500 nm wavelength preferably +5 nm. Respective attenuators 106A and 106C attenuate the individual filtered light components in accordance with desired ratios selected by operator 122 via controller 100. In one aspect of the present embodiment, the attenuator settings are adjusted differentially such that the total luminance output (the attenuated components combined) is equal to a constant. For example, assume that the combined luminance for the 407 nm wavelength light and the 500 nm wavelength light is to be equal to one, and that the originating luminance incident upon respective attenuators is likewise equal to one. If attenuator 106A provides an attenuation level of 0.7, attenuator 106C should therefore provides an attenuation level of 0.3 so that the resulting luminance output for the combined components is equal to 1.0.

The outputs from attenuator 106A and attenuator 106C are brought together by mixer 108A whereupon the resulting mixture is then attenuated by attenuator 110A which is controlled by controller 100. So while attenuators 106A and 106C provide the ratio of spectral components to be summed by mixer 108A, attenuator 110A on the other hand attenuates the combined light mixture until a desired combined power is measured by meter 112 (note that meter 112 may be separate from the instrument).

In producing this first light mixture, the 407 nm wavelength light and 500 nm wavelength light are summed together while no component is provided by the 440 nm wavelength light. Accordingly, controller 100 disables light source 102B as incident upon filter 104B, or alternatively provides full level attenuation by attenuator 106B so that there is no 440 nm wavelength light supplied to mixer 108A. Furthermore, if it is necessary to measure the power of the first light mixture as supplied to the first portion 118 of photometer field 114, then controller 100 can disable light sources 102D and 102E, or alternatively provide full attenuation to attenuator 110B while meter 112 takes a power measurement of the light projected onto photometer field 114.

When it is necessary to provide a light mixture of 440 nm wavelength light and 500 nm wavelength light, light sources 102B and 102C are enabled for providing white light incident upon filters 104B and 104C. Filter 104B filters the white light of light source 102B to provide 440 nm wavelength light, preferably at a λ-max of 440 nm+5/−1 nm. Filter 104C filters the white light of light source 102C to output 500 nm wavelength light as described hereinbefore.

Controller 100 provides a ratio for the 440 nm wavelength light with respect to the 500 nm wavelength light via the attenuation settings of attenuators 106B and 106C. The 407 nm wavelength light component is turned off by either disabling light source 102A or providing full attenuation by attenuator 106A. Mixer 108A mixes the attenuated 440 nm wavelength light from attenuator 106B and the attenuated 500 nm wavelength light provided from attenuator 106C whereupon the resulting mixture is attenuated by attenuator 110A. Again, attenuator 110A is controlled by controller 100 to assure a desired output power as measured by meter 112. The above two illustrated examples characterize the optical channels required for generating the Pair I and Pair III light mixtures respectively irrespective of polarization.

To generate the Pair II light mixture, the lower optical mixing chain is operated in a manner similar to the upper optical mixing chain. Light sources 102D and 102E provide white light incident upon filters 104D and 104E respectively. Filter 104D filters the white light of light source 102D to provide an output wavelength light centered at 480 nm preferably ±1 nm at peak. Filter 104E filters the white light of light source 102E to provide an output wavelength light centered at 580 nm preferably ±1 nm at center. The 480 nm wavelength light is incident upon attenuator 106D while the 580 nm wavelength light is incident upon attenuator 106E. Controller 100 adjusts the attenuation ratios between attenuators 106D and 106E, preferably in a differential manner with respect to one another, such that the total output luminance of the two components combined is equal to a constant. The attenuated 480 nm wavelength light component and the 580 nm wavelength light component are combined by mixer 108B to produce a resulting output light mixture incident upon attenuator 110B. Controller 100 sets the attenuation level of attenuator 110B so that the light incident upon a second portion 120 of photometer field 114 has a predetermined power. Note that to measure the power levels of the Pair II light mixture components, the Pair I and Pair III light mixtures are disabled so that meter 112 measures only Pair III mixture light components as incident upon the second portion 120 of photometer field 114. The controller can turn off the Pair I and Pair III light mixtures by disabling light sources 102A, 102B, and 102C or alternatively by providing full attenuation by attenuators 106A, 106B, and 106C and/or providing full attenuation by attenuator 110A. Thus, photometer field 114 only receives light of the Pair II light mixture which is measured by radiometer 112.

In taking power measurements of the light components of a given light mixture, only one light wavelength component is enabled at a time while meter 112 obtains a power measurement (watts). To obtain the associated luminance value for the light component, the measured power is divided by the illuminated area of the photometer field and multiplied by a luminosity coefficient as associated with the wavelength of the light component as described hereinbefore, supra page 27. The luminosity coefficient is related to the human luminous efficiency characteristics with respect to wavelength of the light.

Figure 8:
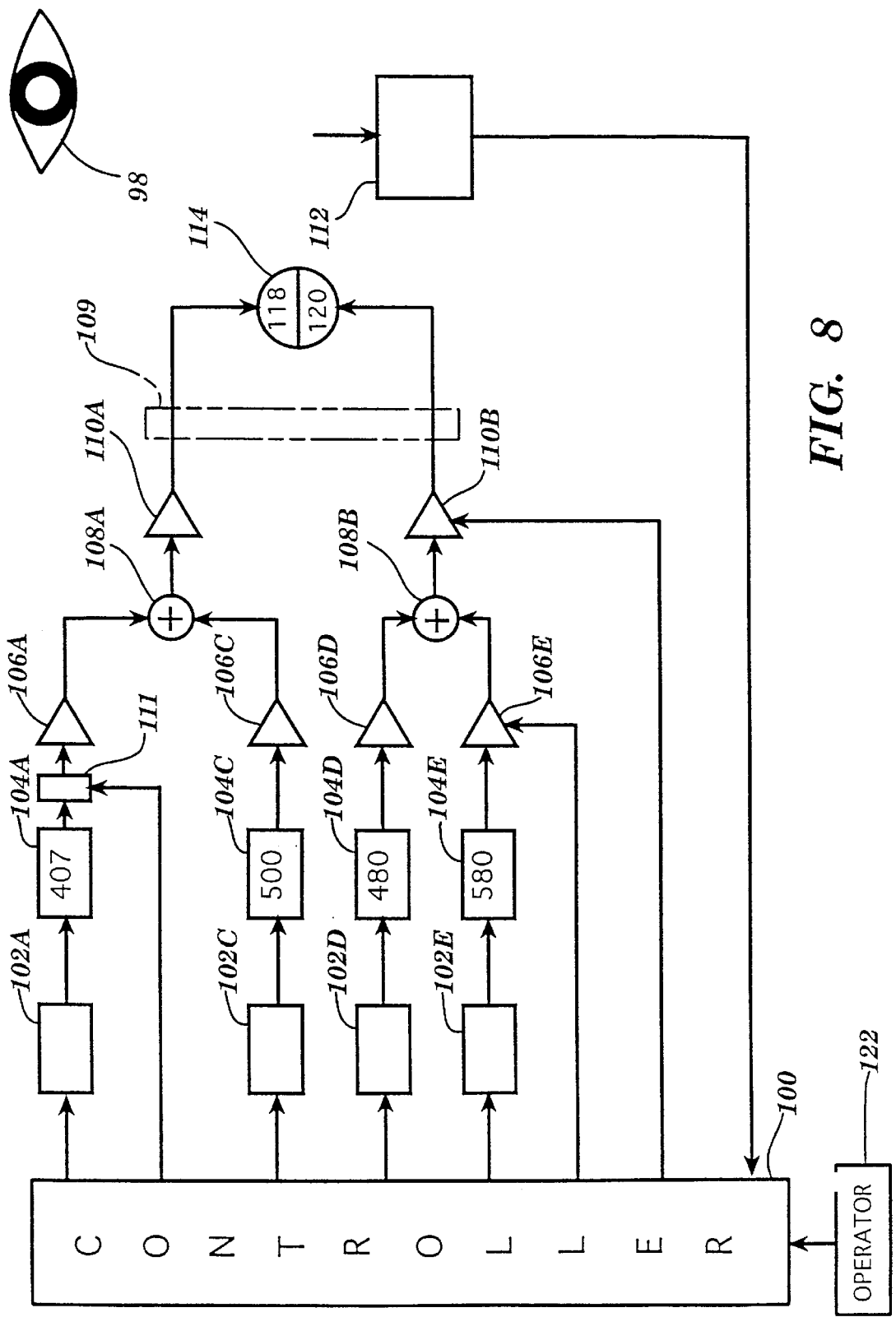
FIG. 8 is a block diagram illustrating an apparatus for assisting an alternative aspect for the method of the present invention.

In an alternative aspect of the present invention, with reference to FIG. 8, a variable electro-optic polarizer 111 is disposed in the optical path of the 407 nm wavelength light (the shorter wavelength light) for controlling the polarization of the 407 nm wavelength light as presented onto photometer field 114. Preferably, electro-optic polarizer 111 is positioned in the optical path of the 407 nm wavelength light after filter 104A and before attenuator 106A. However, one skilled in the art will understand that electro-optic polarizer 111 could be positioned just before filter 104A or after attenuator 106A so long as it affects the polarization of only the 407 nm wavelength light.

Figure 9:
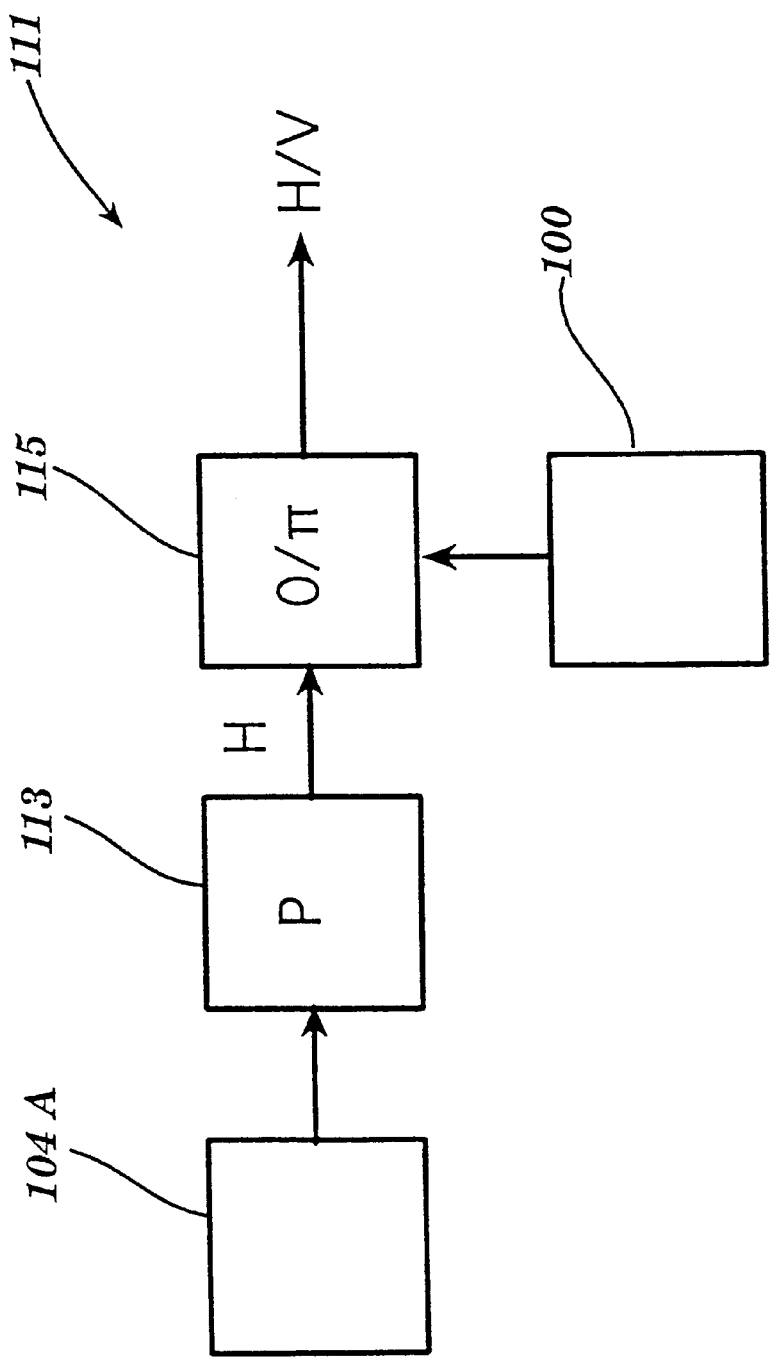
FIG. 9 is a block diagram illustrating a variable electro-optic polarizer.

Electro-optic polarizer 111 preferably comprises, with reference to FIG. 9, a neutral density polarizer 113 followed by a variable pi-cell 115. Neutral density polarizer passes light of one polarization, e.g. horizontal H, to analyzer 115. Analyzer 115 receives the polarized light from polarizer 113 and provides essentially no effect on the polarization of the light, or changes the polarization of the polarized light from the horizontal to vertical, so long as the light is within a given bandwidth as associated with the analyzer. Polarized light may be thought of as comprising two components of opposite circularly polarized light, i.e. left circular polarization $e^{jwt}$ and right circular polarization $e^{-jwt}$. The analyzer comprises an electro-optic crystalline material that has different velocities for right circularly polarized light and left circularly polarized light propagating along a given axis thereof, when the crystalline material is under the influence of an applied electric field. Absent an applied electric field, the velocities for the two separate circularly polarized lights are assumed equal. Assuming light of a given frequency, an electro-optic crystalline material (i.e. analyzer) of a given thickness, and an associated applied electric field across the analyzer; a retardation of $\pi$ radians (180°) can be provided for one of the circularly polarized lights relative the other. Under such circumstances linearly polarized light passing therethrough will have its polarization altered by 90°. Such a variable electro-optic polarizer is available from Oriel Corporation. Alternatively, electro-optic polarizer could be a mechanically rotated polarizer.

Variable optical polarizer 111 receives 407 nm wavelength light from filter 104A and polarizes the light exiting therefrom in accordance with a control voltage received from controller 100. Preferably, variable optical polarizer passes linearly polarized light of either horizontal or vertical polarization in accordance with the control voltage received from controller 100.

As described hereinbefore, respective attenuator pairs of either the upper optical mixing path or the lower optical mixing path are differentially operated to provide constant luminance outputs for the resulting mixture. However, once a close match is established between respective light mixtures, the operator is allowed limited individual control of the separate attenuators (via the controller 100) so that the patient observing the photometer field 114 is able to adjust the attenuators for obtaining an exact match between the respective color mixtures as incident upon the first and second regions 118,120 respectively of photometer field 114.

In a preferred embodiment of the present invention, light sources 102 are Tungsten Halogen light(s) for providing white light to respective filters 104. It will be apparent to one skilled in the art, that individual light sources 102A, 102B, 102C, 102D, 102E could be replaced by a single white light source with individual light paths to the various filters so long as the intensity of white light provided to the respective filters 104 is stable. Such light sources are available from General Electric, Nela Park, Cleveland, Ohio.

Filters 104 are quarter wavelength dielectric layered interference filters that receive white light and pass a spectral light component thereof in accordance with the thickness of the quarter wavelength dielectric layers of the interference filters, and have a peak pass band response that can be shifted slightly by changing the angle of inclination of the filter's surface with respect to the incident light. Such interference filters are readily available from Corion Corp. Alternatively, the filters are monochromators which break white light into narrow bands of particular wavelength components. Such monochromators are available from Spex Industries, Inc. It will be understood to one skilled in the art, that light sources 102 and respective filters 104 could be replaced with other means for producing spectrally pure light, such as a laser source with appropriate diffusion (coherence breaking) and polarization means.

The attenuators are standard variable attenuators such as neutral density wedges as are available from Oriel Corp., Stratford, Conn. Again, the respective attenuators should have incremental adjustments of less than 4% neutral density and preferably are continuously adjustable attenuators.

A skilled artisan will know that additive mixing of colored lights may be accomplished by several means. Any of these means will satisfy the mixing requirements for the light channel associated with attenuator 110B (FIG. 8). The same artisan will know that some of these mixing methods that may be satisfactory for use in the 110B channel, e.g., an integrating sphere or a similar optical device, will not be satisfactory for mixing light for the channel associated with attenuator 110A. Such mixers, as the integrating sphere, do not maintain the polarization of light inducted by polarizer 111 once it has entered and exited.

Figure 10:
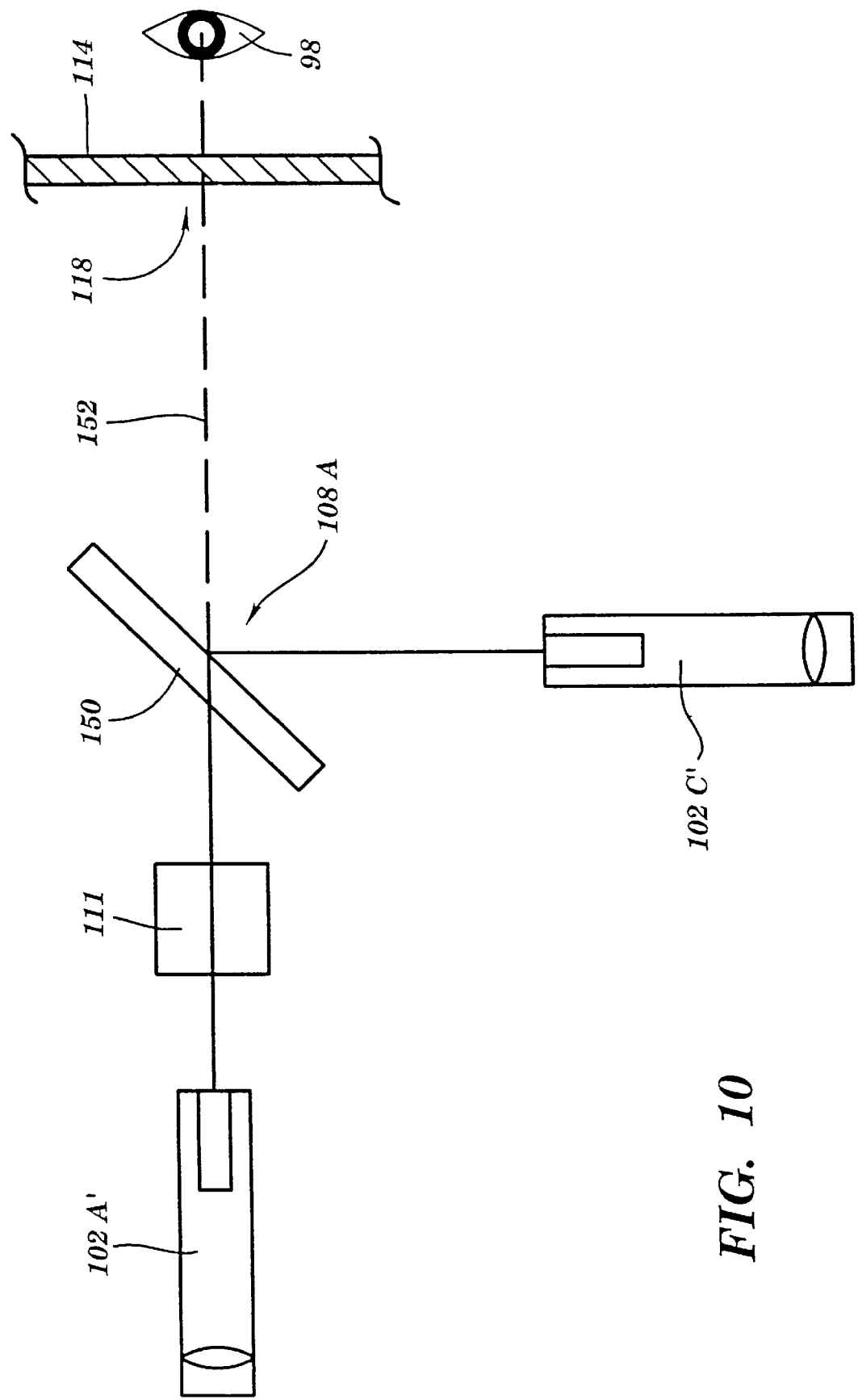
FIG. 10 depicts an apparatus for additive mixing of two lights 102A' and 102C' in which the polarization angle produced by element 111 is maintained to the extent of 96% at the eye of the patient 98.

In a preferred embodiment of the present invention, mixer 108A preserves the polarization angle of light reaching the patient's eye by 96% or more, as measured by the power of the light reaching a radiometer located where the patient's eye 98 would be (i.e., beyond 114). Such a mixer arrangement 108A is shown in FIG. 10, where the mixing is accomplished by a beam splitter 150 that redirects the light of two coaxial congruent projection light sources 102A', 102C' to a common focus at a given distance onto a (finely ground) glass screen, photometer field 118. One half of the bipartite photometer field 114 receives the redirected light 152 from mixer 108A. The beam splitter 150 consists of a glass plate that is strain-free and inclined at 45° to the light projection axis of projector 102A. In this arrangement more than 96% of the light from projector 102A sustains the polarization angle produced by polarizer 111 after passing through screen 118 on its way to the patient's eye.

In the preferred embodiment of the present invention, before photometer 114 and after the two mixers 108A,108B, a beam chopper 109 (FIG. 8) is interposed which presents the different light mixtures of mixers 108A,108B onto respective portions photometer fields 118 and 120 with light inputs that are chopped 180° out of phase with respect to each other. The integration qualities of the eye of an observer are such that the chopping condition of the light is not noticeable so long as the light is chopped at a rate above the flicker fusion rate. By providing alternative light mixture projections onto respective portions 118,120 of photometer field 114, the instantaneous perception of one color mixture of one field will not be influenced by photoluminescence in the lens as might be caused by a primary light of the mixture as projected onto the other field.

Figure 5:
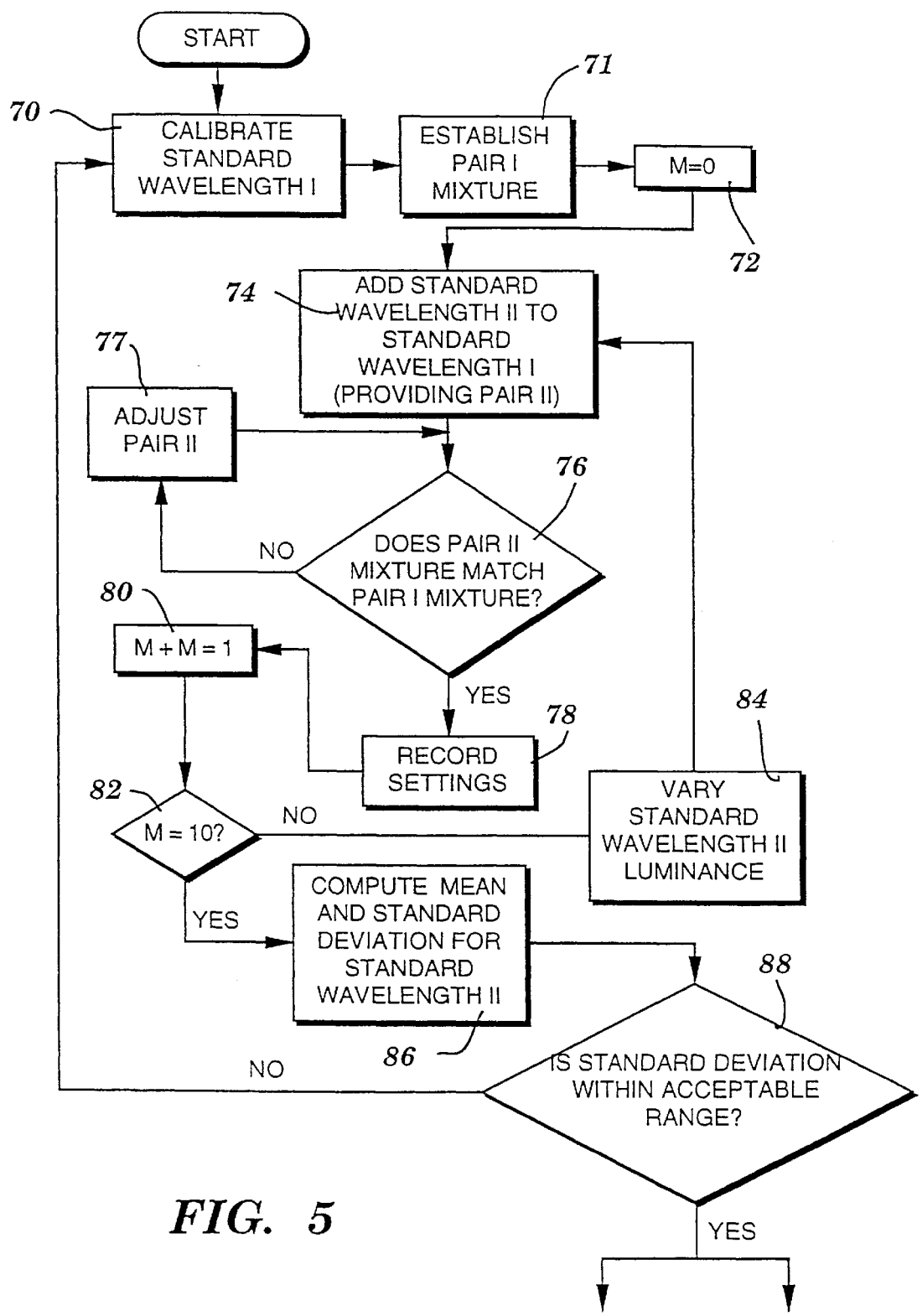
FIG. 5 is a partial flow chart illustrating a method in accordance with the present invention for determining a disease state in an eye of a patient.
Figure 6A:
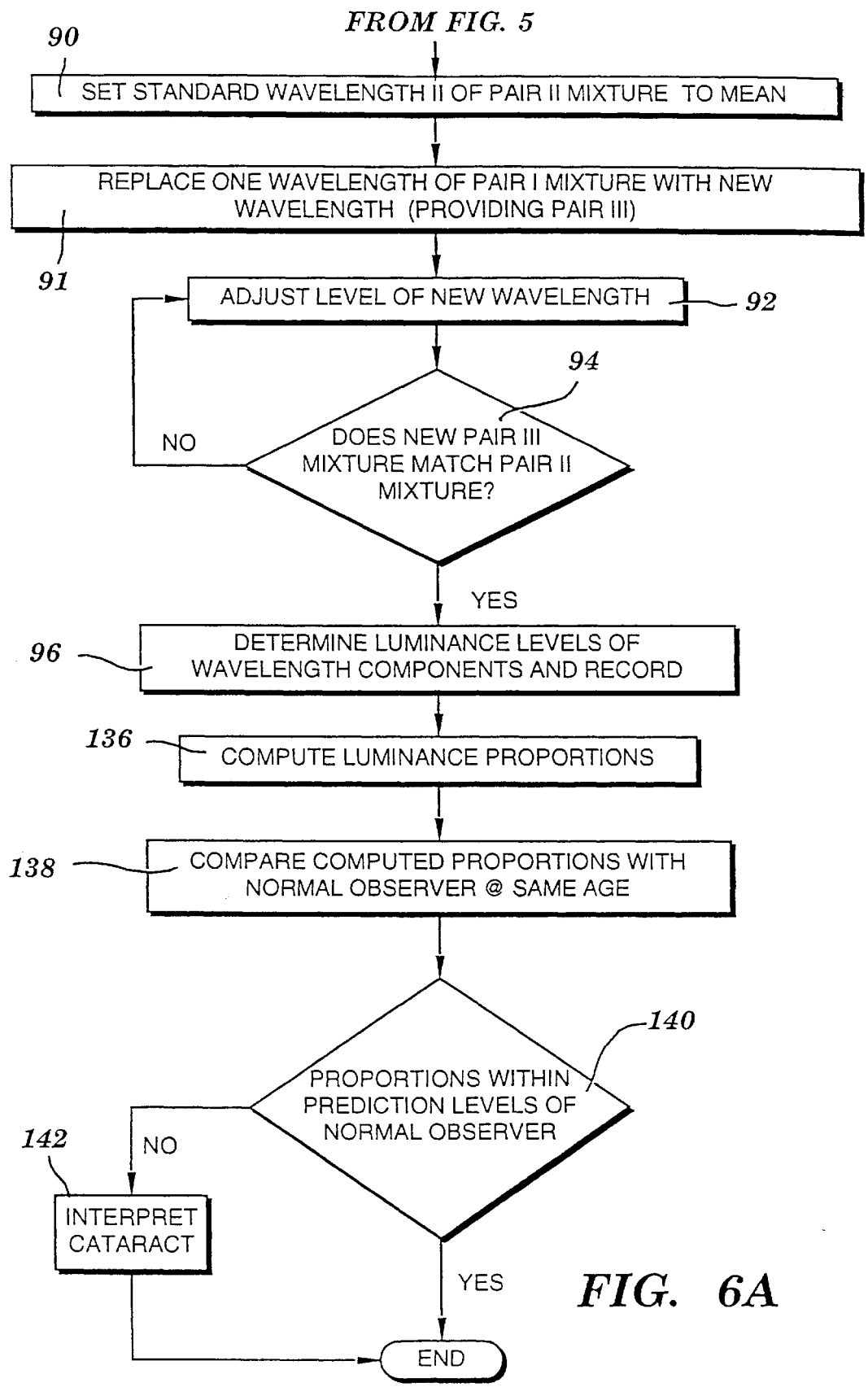
FIG. 6A is a continuation of the flow chart of FIG. 5 illustrating one aspect for the method of the present invention.

With reference to FIGS. 5 and 6a, a first method of the present invention is provided for determining a cataract or a cataract precursor condition of a patient. In step 70, the test apparatus is calibrated for light of a standard wavelength I. To initiate step 70, an operator signals controller 100 (of FIG. 7) to provide 480 nm light, standard wavelength I, onto second portion 120 of photometer field 114. Controller 100 responds by turning on light source 102D and adjusting attenuators 106D and 110B for providing a given luminance of the 480 nm wavelength light on the second portion of photometer field 114. During this calibration adjustment, all other attenuators are set to their full attenuation settings and/or the light sources 102A–102C and 102E are disabled. Next, an integer M is set to an initial state of 0, step 72.

With the light of standard wavelength I properly adjusted, a light mixture, i.e. Pair I, is projected onto the first portion 118 of photometer field 114. The Pair I light mixture comprises an additively mixed combination of 407 nm wavelength light and 500 nm wavelength light as provided via respective optical paths. The patient views photometer field 114 as controller 100 adjusts (per operator inputs) the attenuation levels of the respective light components until the Pair I light mixture, as incident upon the first portion 118 of the photometer field 114, has a hue corresponding to the hue of the 480 nm light, as projected onto the second portion 120 of photometer field 114, as observed by the patient. Once the hue of the Pair I light mixture matches most closely the hue of the 480 nm light, the patient under test signals the controller to record and set the various attenuator settings of the optical path associated with the Pair I light mixture, i.e. attenuators 104A, 104C and 110A, thus establishing the Pair I mixture (step 71).

It is assumed that the apparatus has been precalibrated so that controller 100 can determine the power level of a given light component reaching photometer field 114 in accordance with its associated attenuator (and polarization) settings. During such precalibration, controller 100 enables one wavelength light component at a time, disabling all other wavelength lights, and calibrates the various attenuator (and polarization) settings in accordance with the power received at photometer field 114 as measured by radiometer 112. Alternatively, controller 100 may repeat respective component power measurements directly as needed instead of indirectly deriving such power levels from the attenuator (and polarization) settings and associated precalibration tables.

Next, in step 74, 580 nm wavelength light, standard wavelength II, is combined with the 480 nm wavelength light, standard wavelength I, so as to desaturate the color of the 480 nm spectral light and provide a Pair II light mixture of color more closely matching that of the previously established set Pair I light mixture. During this operation, controller 100 adjusts (step 77) the attenuator settings of attenuators 106D and 106E in preferably a differential manner until the saturation level of the Pair II light mixture (as projected onto the second portion 120 of photometer field 114) corresponds to the saturation provided by the Pair I light mixture (as projected onto the first portion 118 of photometer field 114). Attenuator 110B is adjusted to obtain the desired total luminance of the Pair II light mixture. When controller 100 provides the required ratio for matching (step 76) most closely the saturation of the Pair II light mixture with the Pair I light mixture, as observed by the patient under test, the patient then signals controller 100 to stop further adjustment. In one embodiment of the present invention, the patient is then permitted limited control of attenuators 106A, 106C, 106D, and 106E until obtaining an "exact" color match. The patient (or clinician conducting the test) then signals the controller to record all of the attenuator settings associated with providing the Pair II light mixture, i.e. step 78. Integer M is then incremented by one in step 80.

In step 82, integer M is examined to determine whether or not it is equal to 10. After a first iteration, M is equal to 1 and system control moves to step 84 wherein the luminance of the 580 nm wavelength light component, standard wavelength II, of the Pair II light mixture is changed randomly, while leaving the luminances of the other three lights fixed. Control moves back to step 74 wherein adjustment of the 580 nm wavelength light is made until obtaining the desired saturation again. The intensity settings of the 580 nm light should be made randomly above and below the last adjustment point, i.e. for providing Pair II light mixtures that are too desaturated and too saturated relative the Pair I mixture. These steps of adjusting the level of the 580 nm wavelength light and re-matching the light mixture of Pair II to the mixture of Pair I are repeated a plurality of times with the respective attenuator settings being recorded after each iteration until integer M is equal to 10. An artisan will understand that the number of iterations to be performed could be a number other than 10 so long as the number of iterations is suitable for statistical purposes to obtain a useful mean and standard deviation thereof. After the tenth iteration, the mean and standard deviation for the power level of the 580 nm wavelength light, standard wavelength II, required for affecting the desired saturation level are computed in step 86 and examined in step 88 to determine whether or not the standard deviation is within an acceptable range. If the standard deviation is not within an acceptable range, it is determined either that the patient has a visual system defect that precludes diagnosis with this method or did not understand the matching procedure, whereupon control transitions back to beginning step 70 so that the process may be initialized and performed all over again to rule out the possibility that the patient has merely misunderstood the matching principles. Alternatively, the testing procedure could be terminated and a message directed to the operator that such termination condition has been reached. It is anticipated that this instrument and method will be effective even for patients with protan and deutan color vision defects and be inapplicable to persons with achromatopsia or tritan defects.

Assuming that the standard deviation calculated in step 86 is within an acceptable pass range, process flow transitions to step 90 (FIG. 6A) wherein the level of the 580 nm wavelength light is set to its mean value as calculated in step 86 and the 480 nm and 500 nm lights are set to the levels associated with the above match. In step 91, the 440 nm wavelength light replaces the 407 nm wavelength light component of the Pair I light mixture for providing a new Pair III light mixture to be incident upon the first portion 118 of photometer field 114. In step 92, the level of the 440 nm wavelength light is then adjusted via attenuator 106B in order to effect a desired mixture in the first portion 118 of photometer field 114 exactly matching the Pair II light mixture as incident upon the second portion 120 of photometer field 114. This adjustment procedure is continued between decision step 94 and operating step 92 until a match is obtained between the respective light mixtures as observed by the patient. Once the match has been obtained, process flow moves to step 96 wherein the luminance levels of the spectral components making up the Pair III light mixture are determined and recorded. In accordance with one aspect of this embodiment of the present invention, the luminance levels are obtained from direct power measurements, obtained by meter 112 with individual light components being directed alone upon photometer field 114. Alternatively, the apparatus is precalibrated wherein controller 100 can determine the luminance levels of individual light components based upon the respective attenuator (and polarization) settings alone.

In step 136 proportions are computed between the light components of the Pair III light mixture and the Pair I light mixture as described hereinbefore. The ratio for the Pair I light mixtures is computed according to the luminance of its 500 nm wavelength light component over the sum of the luminance of the 407 nm and the 500 nm wavelength lights. The ratio computed for the Pair III mixture is equal to the luminance of its 500 nm wavelength light component divided by the sum of the luminance of the 500 nm wavelength light component and the 440 nm wavelength light. The luminance value of each wavelength light component is determined by multiplying the power level of the component by a luminosity coefficient associated with the components wavelength as described hereinbefore, supra page 27.

Groups of observers (subjects) who have no cataracts and who belong to a single demographic group, e.g. Oriental women with dark eyes, African (American) men with very dark eyes etc., are used to develop separate standardization groups. As in FIG. 3, their ages need to cover a broad range of ages, especially the 60–85+ that constitute the ages of those most likely to be tested for senile cataract. Similarly, patients from each of these groups who have surgically extracted or surgically mature cataracts are employed to provide validation data for each demographic group.

In step 138, the computed ratios for the patient under test are compared to corresponding ratios of subjects without identified cataracts of an age matching the patient under test. It is then determined whether or not the computed ratios are within a given prediction interval of the ratios for those without cataracts, per step 140. If the computed ratios are below the prediction interval of this group, then an interpretation is made regarding the cataract condition of the patient (step 142) and reported to the clinician conducting the test. If the ratios are within the prediction level of this group, then controller 100 reports an absence of cataracts for the patient and terminates the test procedure.

In a first alternative aspect of this embodiment of the present invention, the computed ratios for the patient are compared to standardized data of a standardization group to provide information regarding the stage of cataractogenesis. The proximity of the patient's computed ratios relative to the predetermined ratios of a juvenile subject, or a subject with an intra-ocular lens, and a mature subject with cataracts indicates the stage of cataractogenesis for the patient between the juvenile stage and the mature stage.

In accordance with a second alternative aspect of this embodiment of the present invention, a rate of cataractogenesis is determined. Employing a predetermined standardized curve that maps ratio values with respect to age for a standardized group, the slope of the standardized curve at a ratio value corresponding to the patient's determined ratio value is taken as representative of the rate of cataractogenesis.

In accordance with a third alternative aspect of this embodiment of the present invention, a determination is made regarding the number of years by which the patient's cataractogenesis is accelerated or retarded with respect to a predetermined standardized curve of a standardization group. A time offset in number of years is determined between the patient's determined ratio value and a corresponding point on the standardized curve. This time offset is taken as the number of years by which the patient's cataractogenesis has been accelerated or retarded, depending upon which side of the curve the patient's ratio value resides.

In accordance with a fourth alternative aspect of this embodiment of the present invention, an estimation is provided of the number of years within which the patient may develop cataracts. An equivalent point is located on a predetermined standardized curve of a standardization group in accordance with the patient's ratio value. The number of years along the standardized curve from the equivalent point to a value thereof associated with cataracts is taken as an estimation of the number of years within which the patient may develop cataracts.

Figure 6B:
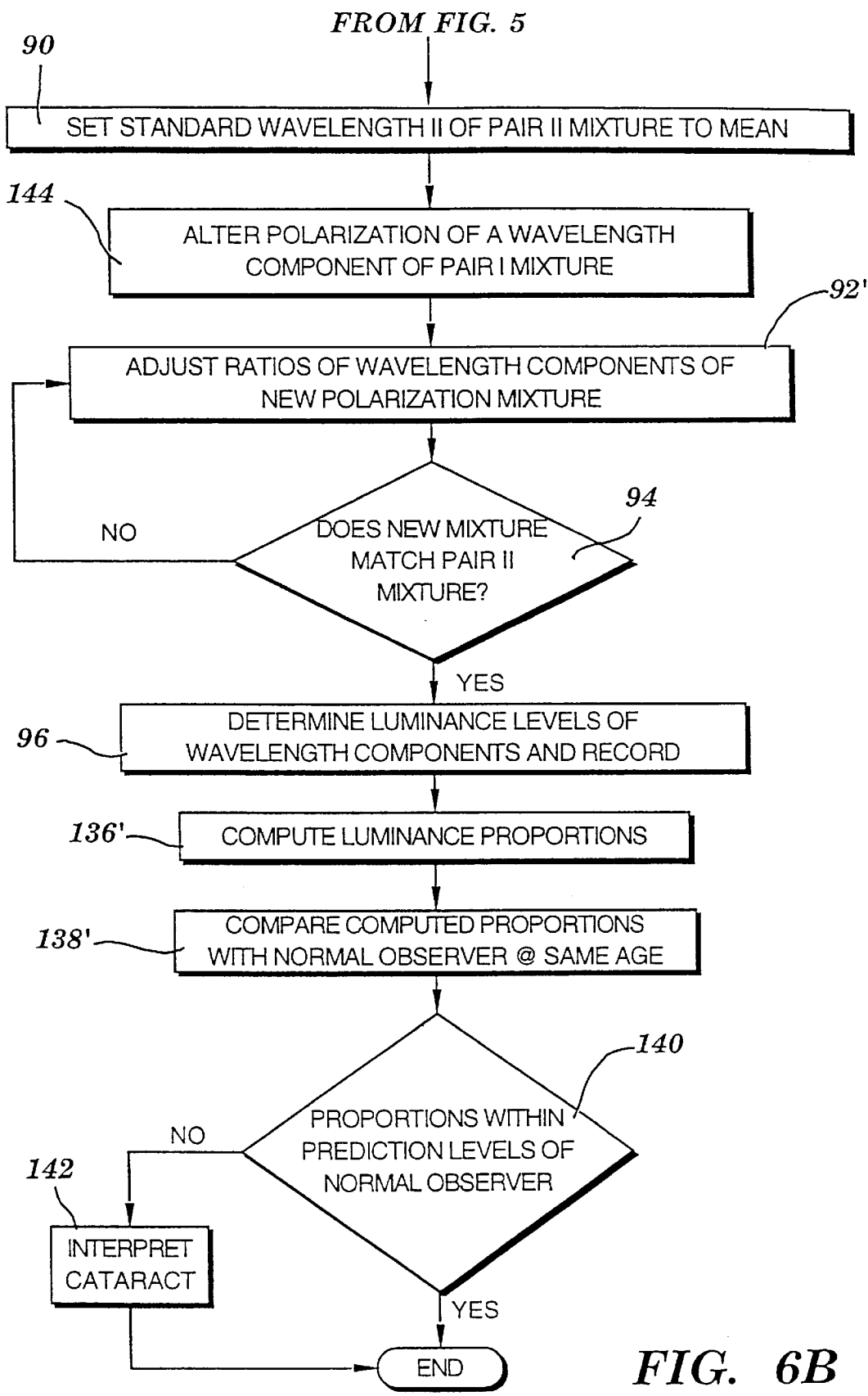
FIG. 6B is a continuation of the flow chart of FIG. 5 illustrating an alternative aspect for the method of the present invention.

With reference to FIGS. 5, 6B and 8, a second method of the present invention is provided for determining a cataract or a cataract precursor condition of a patient. Steps 70 through 90 are performed in the same manner as described hereinbefore except that the 407 nm wavelength light component of the Pair I mixture is linearly polarized by variable electro-optic polarizer 111 (FIG. 8) in either H or V mode. Controller 100 sets the control voltage to variable electro-optic polarizer 111, which is in the optical path of the 407 nm wavelength light, so as to linearly polarize the 407 nm light in a first polarization state, i.e., either vertically or horizontally.

Assuming the patient is able to consistently provide color matches between the Pair I light mixture and the Pair II light mixture, such that the standard deviation calculated in step 86 is within an acceptable range as examined in step 88, then control transitions to step 90, with reference to FIG. 6B, wherein the level of the 580 nm wavelength light is set to its mean value as calculated in step 86. Next, in step 144, the polarization state of the 407 nm wavelength light component of the Pair I light mixture is changed, e.g., from horizontal to vertical or vice versa. Controller 100 changes the control voltage applied to variable electro-optic polarizer 111 so that it imparts a second polarization state to the 407 nm wavelength light.

The levels of the new Pair I light mixture, having the 407 nm wavelength light component of the second polarization state, are adjusted per step 92' via attenuators 106A and 106C until the new light mixture (in the first portion 118 of photometer field 114) matches, per step 94, the Pair II light mixture (as incident upon the second portion 120 of photometer field 114) as observed by the patient under test. Once the color match has been obtained, control transitions to step 96 wherein the luminance levels of the new polarized 407 nm wavelength light and the 500 nm wavelength light components of the new Pair I light mixture are determined and recorded. Again, the levels of the various light components can be determined by direct measurements using meter 112, or indirectly in accordance with respective attenuator (and polarization) settings and respective predetermined calibration tables as described hereinbefore.

In step 136', respective ratios are computed between the light components of the original Pair I light mixture (having the 407 nm wavelength light of the first polarization state) and the new Pair I light mixture (having the 407 nm wavelength light of the second polarization state). The ratio for the original Pair I light mixture is computed according to the luminance of its 500 nm wavelength light component divided by the sum of the luminance of the 407 nm wavelength light component of the first polarization state and the 500 nm wavelength light. The ratio computed for the new Pair I mixture is equal to the luminance of its 500 nm wavelength light component divided by the sum of the luminance of the 407 nm wavelength light component of the second polarization state and the 500 nm wavelength light. Again, the luminance levels are preferably computed according to the product of determined power levels and associated luminosity coefficients as described hereinbefore, supra page 27.

In step 138', the computed ratios are compared to corresponding ratios of a standardization group of age matching the patient under test. Such standardizations and validations are required for the different polarization angles as well. It is then determined in step 140 whether or not the computed mixture proportions are within a given prediction interval of the proportions for the standardized group, and an appropriate cataract interpretation (step 142) is reported to the clinician conducting the test similarly as described before.

In both methods of the embodiments described hereinbefore, again it is preferable that the light mixtures as incident upon respective photometer fields 118 and 120 be incident in alternating sequence so that light of one mixture will not affect the patient's perception of the other mixture. As described in a previous embodiment, such alternating sequencing of light mixture can be provided by chopper 109.

It will be understood that some patients will require corrective lenses. Accordingly, the apparatus and methods of the present invention should provide standard trial lenses for correcting subject vision with materials that do not significantly differentially absorb nor photoluminesce under the influence of the spectral lights employed within the present invention.

It will be understood that many changes to the elements of system 96 are possible by one skilled in the art. For example, attenuators 106 and/or 110 may be neutral density filters under patient, operator and/or microprocessor control. Also, in some instances, light mixtures of Pair I and Pair III could be matched directly in one step, eliminating the preliminary match between the mixtures of Pair I and Pair II.

The Pair I and Pair III ratios obtained using the 407+500 nm and the 440+500 nm mixtures respectively, both vary with patient and lens thereof. However, the Pair I and Part III ratios are differentially affected by the cataractogenic process. Perturbations in the 407+500 nm Pair I mixture with age are more pathognomonic of the two, and accordingly are used for diagnosis and assessment of a disease as described hereinbefore. This differential effect is presumed to be due to the fact that this mixture of wavelengths is selected to capitalize on a well-identified lens fluorophore. However, perturbations due to cataractogenesis also occur, but to a lesser degree, in the 440+500 nm Pair III ratios. Accordingly, further test methods determine the perturbation differentials between the Pair I and Pair III ratios, and employ them for differential diagnoses. Suitable standardizations and validation data for these differential diagnosis must be available for use in this manner.

With reference to the FIGS. 11–14, yet another method of the present invention is provided for determining a cataractogenesis state of a lens of a patient. This method obtains excellent results because it employs a patient's ability to more easily, quickly and reliably determine color differences between a pair of lights displayed on a photometric field. The new method greatly simplifies the task since the patient is only required to make comparative judgments between two stimuli on a single color difference dimension at any one time, e.g., of hue or of saturation or of brightness. In contrast the previous methods require the patient to adjust the instrument by a method of successive approximations of brightness, of hue, and of saturation to reach an exact color match or "real" match. The former methods use the patient's capacity to identify the condition of color differences to guide the specific adjustments toward a no difference condition. Analogously, by using a patient's capability to identify color differences, this new method encompasses the subject matter of the previous methods. However, the new method utilizes the teachings and results of the previous methods to reduce the total number of steps (i.e., adjustments by the patient) required to determine a disease state, such as cataractogenesis, in the eye of a patient.

In a preferred embodiment of the present method, the apparatus disclosed herein (FIGS. 7 and 8) is utilized. Referring to FIG. 14, a first step 226 comprises compiling a series of computed luminance values for various light components comprising the pairs of metameric lights, taught herein such as at step 96 in FIGS. 6A and 6B. These luminance values may then be utilized to compute luminance ratios or proportions, taught hereinabove such as at step 136, 136' in FIGS. 6A and 6B. Further then, these proportions may be compared to various standardization groups so that the existence and stages of cataractogenesis may be determined. The standardization groups could be based on various factors, such as, patients with different stages of cataract formation from surgically ripe cataract to normal to an intra-ocular PMMA lens, eye color, complexion, gender, certain diseases (e.g., diabetes), or other cataract risk factors, of the group.

Figure 12:
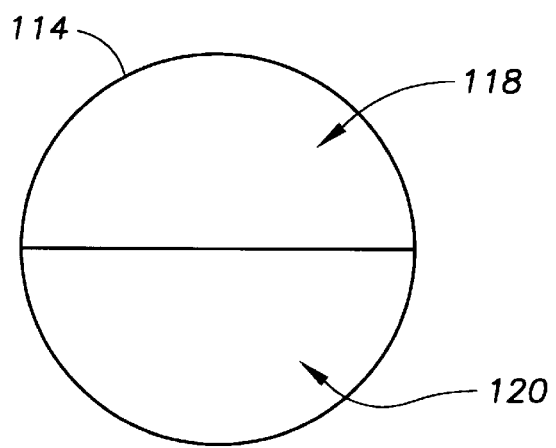
FIG. 12 is a photometer field similar to that in FIGS. 7 and 8.

Although various pairs of spectral lights may be utilized, excellent results are obtained when the pair of metameric lights comprise 410 nm mixed with 510 nm as Pair I (the principal light) in half 120 of field 114 of FIG. 12, and 480 nm mixed with 580 nm as Pair II (the select light) in half 118 of field 114. Also, although various components may comprise the light pairs for the metameric lights, it is preferred that these lights comprise a light mixture of at least two different wavelength components and each light has at least one component that is different from the other components making up the pair of lights.

In a next step 227, the Pair I and II pairs of lights are projected upon the field 114, one at 118 and one at 120. The patient then compares the two lights and responds in terms of a qualitative difference between the lights. This qualitative difference is referred to herein generally as a color dimension such as brightness, hue or saturation, and specifically, as a measure in terms of a "too this" or "too that" statement by the patient (e.g., where "this" or "that" is violet, green, bright, dark, white or pure). This color difference is quantifiable at each increment of adjustment because it is determined by a particular light component and its associated luminance value in relation to pairs of components, explained hereinabove in relation to the series of computed luminance values.

Now, the patient signals an operator of the apparatus how a select light as compared to the other light appears to have "too much" or "too little" of one of the three dimensions. The operator responds by adding to or subtracting from the light intensity of a component of the select or principle light to make it appear less distinguishable from the other light on a particular color dimension. That is, utilizing the series of computed luminance values for various pairs of metameric lights, the operator adjusts 228 the luminance level of a particular component of the select or principal light in a measured increment towards making a color difference dimension measure of the select and principal lights less distinguishable. Ideally, the increment will comprise a series of such increments varying from "coarse" to "fine" adjustments to enable the operator to selectively narrow the difference(s) between the pair of lights.

The adjusting is continued for a number of increments, and preferably in a rapid manner to best utilize the patient's comparative abilities with minimal interruptions, so that the difference between the two lights is no longer as great. Then, once the patient reports that the color difference dimension measure of the select light changes from a "too this" color difference dimension measure to a "too that" color difference dimension measure, the adjusting is terminated.

At this time, the disease state of the eye of the patient can be determined. Specifically, when the color difference dimension measure changes from a "too this" to a "too that" a transition range can be established in step 229, comprising the last two measures such as at 220 and 222 in FIG. 11. Accordingly, because the luminance values associated with 220 and 222 are known, the luminance proportions or ratios are likewise predetermined. Thus, the ratios then need only be readily compared, step 230, to existing standardization data and a disease state of the eye is determined, step 231. With the predetermined ratios, the disease state determinations are made as taught hereinabove for the previous methods concerning measurement theory, scaling theory and psychometric methods.

Alternatively, a transition range match point could be inferred, based on the fact that a "real" match point (as match point is defined hereinabove in the previous methods) exists somewhere in the transition range. Here, a transition range match point is defined as inferring where the "real" match point is, based on color difference dimension measures only, which does not ultimately establish a "real" match point. Then, by approximating ratios in the transition ranges, corresponding to the transition range match points, one can easily compare these ratios to data from a standardization group and determine the disease state.

Under either discussed ways for determining the disease state, the determining is preferably accomplished without requiring the patient to actually make a "real" match. Further, by using predetermined ratios and luminance values the whole method is substantially expedited.

Although various wavelength spectral light components may be utilized and they may be adjusted or varied in any order to compare a specific color difference dimension (brightness, hue or saturation), experimentation has determined that certain light components of certain frequencies have a more significant effect on certain color difference dimensions. For example, consider 510 nm light with its green hue and 410 nm light with its violet hue. When these two lights are mixed, adding 410 nm light to the 510 nm light more significantly changes the hue created by the pair of lights than it does the brightness contributed by the 510 nm light alone. In a similar fashion, 580 nm light added to 480 nm light more significantly effects a saturation of the combination than it does the other color difference dimensions of hue and brightness. On the other hand, 480 nm light added to 580 nm light more significantly effects brightness of the combination than it does the other color difference dimensions.

Figure 11:
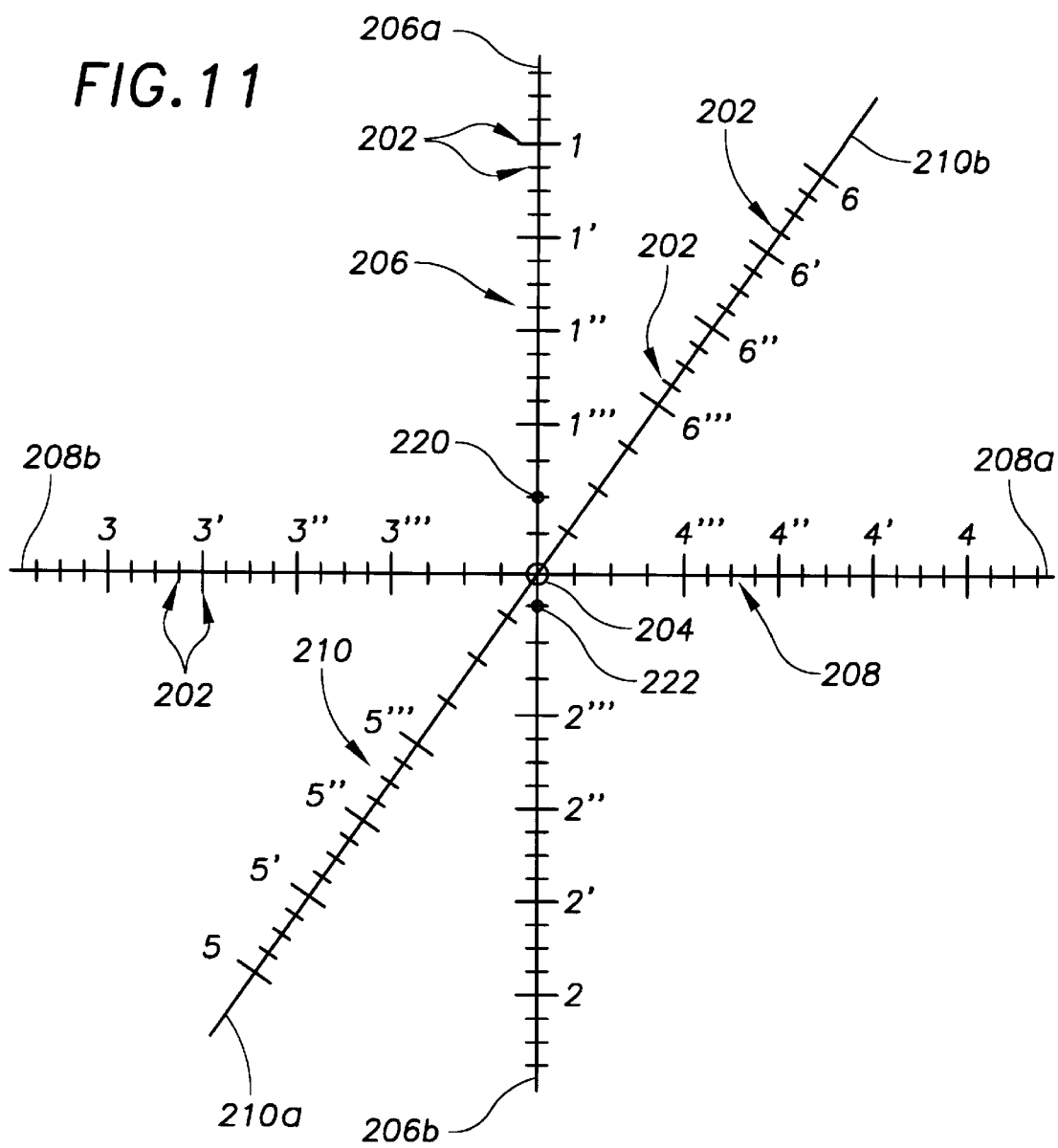
FIG. 11 is a graph depicting spectral pairs of metameric lights that have predetermined luminance values and ratios corresponding to color difference dimensions of brightness, hue and saturation.

For example, referring to FIG. 11, take the color difference dimension being evaluated by the patient as that of brightness on axis 206. Further, consider the pair of metameric lights comprising 410 nm mixed with 510 nm as Pair I (the principal light) in half 120 of field 114, and 480 nm mixed with 580 nm as Pair II (the select light) in half 118 of field 114. If the select light compared to the principal light is determined to be "too bright", for example at 1', then the intensity of the 480 nm component is adjusted or varied a predetermined increment to make the select light "less bright", for example closer to "real" match point 204, but still brighter than the principal light. Once the color difference dimension measure of the select light changes from a "too bright" 220 evaluation to a "too dim" 222 evaluation, the last evaluated luminance values 220, 222 corresponding to the color difference dimension measures in each part of the axis 206 are recorded. One can then determine the disease state based on either values associated with points 220 and 222 or by alternatively inferring that the transition range match point of the color difference dimension exists in between 220 and 222.

FIG. 11 represents, in three dimensional space, each of the three color difference dimensions that correspond to luminance values for a pair of metameric lights. The point 204 would be a "real" match point that establishes in color space where the ratio of the light components of a first pair would appear identical to a second pair. For example, if the pairs of metameric lights comprise 410 nm light with 510 nm light (Pair I) and 480 nm light with 580 nm light (Pair II), then the following observations are represented for a patient, regardless of a disease state, if any.

The patient observes that the luminance values along the 206$a$ side of the 206 axis make Pair II "too bright" compared to Pair I. In contrast, the luminance values along the 206$b$ side of the 206 brightness axis make Pair II "too dim" compared to Pair I. Also, the patient observes that the luminance values along the 208$a$ side of the 208 hue or chromaticity axis make Pair I "too violet" compared to Pair II. In contrast, the luminance values along the 208$b$ side of the 208 axis make Pair I "too green" compared to Pair II. In this example with these particular Pair I components, the 208 axis is referred to as the violet-green axis, which happens to correspond to the colors of these components as viewed by a normal trichromat. Finally, the patient observes that the luminance values along the 210$a$ side of the 210 saturation axis make Pair II "too saturated" (or blue) compared to Pair I. In contrast, the luminance values along the 210$b$ side of the 210 axis make Pair II "too dim" (or white) compared to Pair I.

Referring to FIG. 13, under the present example once a transition range is established along any one axis 206, 208 or 210, the luminance values associated with the pair of metameric lights and their corresponding ratios or proportions, all which are predetermined as taught hereinabove, can be compared to data from a standardization group. FIG. 13 is a graph representing a compilation of predetermined luminance ratios calculated from "real" match points, i.e. along all three color difference dimension axes. Here, curve 215 represents the control curve for a patient with normal cataract formation for their age, and point 214 would be the ratio corresponding to a "real" match point for the patient having a normal predisposition to cataract formation at approximately age 55, for example. Curve 213 represents the curve for pseudophakic patients who have had a cataractous lens removed and replaced by an intra-ocular PMMA lens. Thus, they have no cataract formation for their age, and point 212 would be the ratio corresponding to a "real" match point for such a patient at approximately age 55, for example. Finally, curve 217 represents the surgically ripe cataract curve for a patient that is about to have a cataract removed, thus, having surgically ripe cataract formation for their age, at point 216.

For example, if the approximated transition range match point is for a 55 year old patient who has a ratio value of about 0.94 corresponding to point 214, the patient will be understood to have a standard cataractogenic rate or predisposition to cataract formation. If the transition range match point is above the point 214 it indicates a slower than standard rate of cataractogenesis. If below the point 214 and statistically above the confidence band of point 216, this indicates an accelerated rate of cataractogenesis. Further, to interpret stages of cataract formation, rate of cataractogenesis, acceleration or retardation of the disease, and estimating the development time of the disease, are all performed in the same manner as taught hereinbefore with the previous methods. Also, it should be noted that the standardization function shown in FIG. 13 is for a group of European-Caucasians. Different standardization functions may be expected from groups having different eye colors or complexions. Different functions might be obtained for the women and the men of those groups also.

While a disease state determination can be made through an evaluation of only one color difference dimension, which establishes one transition range and effectively ignores other transition ranges, in certain situations it may be necessary to look at two or three color difference dimensions. It should be understood that to evaluate one or more color difference dimensions would be accomplished similarly to that for brightness axis 206, but varying the particular light components that more significantly affect the other color difference dimensions. Also, although any of the color difference dimensions could be evaluated to make a disease state determination under this method, excellent results are obtain when the "violet-green" hue axis 208 is employed with the Pair I light components alone.

Further, if desired, such an evaluation could be performed using three axes and the results compared using a nomographic type chart to determine the disease state. The nomogram would be constructed and analyzed as one skilled in the art of graphic representation would do.

Returning to FIG. 11, another explanation is offered in the form of a proof for the sample Pair I and Pair II light components, based on application of the methods taught previously hereinabove. Starting with only the 510 nm light, it is projected upon one half of the field 114 and adjusted to be a comfortable brightness, as observed by a patient. Next, 480 nm light is projected on the other half of the field 114 and it is adjusted to equal brightness of the 510 nm light, establishing a match along the brightness axis 206. Then, 410 nm light is added to the 510 nm light and adjusted to match the hue of the 480 nm light, establishing a match along the hue axis 208. Finally, 580 nm light is added to the 480 nm light and adjusted to match the saturation of the 410 nm and 510 nm mixture, establishing a match along the saturation axis 210.

With all three axis matched, a "real" match point 204 is determined. By corollary then, it is clear that when adjusting the mixture results along any color difference dimension, and a patient indicates a change from a "too this" to a "too that" observation, the match point 204 must exist in between. In this way, this last method utilizes the teachings and available results of the previous methods. Then, this method goes forward to provide simpler steps that accomplish essentially the same result, but, in the form of differences that define a transition range rather than the form of exact similarities that define a match point. With transition range information, ratios can be established and a disease state determined, all as taught hereinabove in this last method.

While several aspects of the present invention have been described and depicted herein, alternative aspects may be effected by those skilled in the art to accomplish the same objectives. Accordingly, it is intended by the appended claims to cover all such alternative aspects as fall within the true spirit and scope of the invention.

We claim:

1. A method for determining a disease state in an eye of a patient, comprising the steps of:
    providing a plurality of metameric lights for viewing by said patient, each of said plurality of lights having an associated color difference dimension;
    comparing a color difference dimension first measure of a principal light of said plurality of lights with a color difference dimension second measure of a select light of said plurality of lights, as reported by said patient;
    adjusting said select light to make said color difference dimension second measure appear less distinguishable from said color difference dimension first measure, as reported by said patient;
    determining said disease state based on a transition range defined by a change between said color difference dimension second and first measures.

2. A method according to claim 1 wherein said adjusting comprises referencing said color difference dimension measures to predetermined data of a standardization group and determining an existence of said disease state in accordance with relative placement of said color difference dimension measures to said predetermined data.

3. A method according to claim 2 wherein said predetermined data is with respect to age, eye color, complexion and gender of said patient and said standardization group.

4. A method according to claim 1 wherein each of said plurality of metameric lights comprises a light mixture of at least two different wavelength components and each metameric light has at least one different component from each other metameric light.

5. A method according to claim 1 wherein each of said plurality of metameric lights comprises a light mixture of at least two different wavelength components and said color difference dimension measures correspond to luminance values and ratios associated with said components.

6. A method according to claim 1, wherein said step of adjusting comprises establishing a match point in said transition range.

7. A method according to claim 1 wherein a correlation to diabetes is provided by referencing said color difference dimension measures to the predetermined data.

8. A method according to claim 1 further comprising said principal and said select lights having a second color difference dimension associated with each;
    comparing a second color difference dimension first measure of either said principal light or said select light with a second color difference dimension second measure of the other of said principal light and said select light, as reported by said patient;
    adjusting said second color difference dimension second measure to make it less distinguishable from said second color difference dimension first measure, as reported by said patient;
    determining said disease state based on a second transition range defined by a change between said second color difference dimension first and second measures.

9. A method according to claim 1 wherein one light of said plurality of lights excites a fluorophore of a lens associated with the eye of said patient.

10. A method according to claim 1 wherein said step of providing a plurality of lights includes providing at least one light of said plurality of lights with a given polarization.

11. A method according to claim 1 wherein said color difference dimension comprises a violet-green spectrum axis.

12. A method according to claim 1 wherein said color difference dimension measures comprise brightness, hue or saturation.

13. A method according to claim 1 wherein said adjusting comprises a combination of coarse and fine increments and adjusting said color difference dimension measures by said increments in narrowing degrees of difference corresponding to data of a standardization group, as reported by said patient.

14. A method according to claim 13 further comprising determining a transition range match point by adjusting said color difference dimension second measure to make it appear indistinguishable from said color difference dimension first measure, as reported by said patient, and determining said disease state based on said color difference dimension measures defining said transition range match point.

15. A method according to claim 1 wherein said transition range is defined by adjusting said color difference dimension measures until one of said color difference dimension measures changes to approximate the other of said color difference dimension measures, as reported by said patient.

16. A method according to claim 1 wherein said step of determining said disease state comprises determining an existence of said disease state.

17. A method according to claim 1 wherein said step of determining said disease state comprises determining an extent of said disease state.

18. A method according to claim 1 wherein said step of determining said disease state comprises determining a development rate of said disease state.

19. A method according to claim 1, wherein said disease state is a cataract and wherein said step of determining said disease state comprises comparing said color difference dimension measures of said transition range to a stage of cataract formation.

20. A method for determining a disease state in an eye of a patient, comprising the steps of:
providing a first light and a second light for viewing by said patient, each of said first and second lights comprising a mixture of at least two lights and having at least one color difference dimension associated therewith;
varying said mixture of said second light to a first set ratio where said patient reports that first color difference dimension measures associated with each of said first and second lights appears less distinguishable;
adjusting said mixture of said first light to a second set ratio where said patient reports that second color difference dimension measures of said first and second lights appear less distinguishable; and
determining said disease state based on said first and second set ratios.

21. A method according to claim 20, wherein said step of determining said disease state comprises interpreting a cataract condition based upon a comparison of said first set ratio and said second set ratio to corresponding set ratios of a standardization group.

22. A method according to claim 21 wherein said comparison is made relative to the standardization group at an age corresponding to an age of said patient.

23. A method according to claim 20 wherein said step of determining comprises interpreting a cataractogenic rate based on said first and second set ratios relative respectively to characteristic curves of a standardization group.

24. A method according to claim 23 wherein said step of interpreting does so on the relative placement of said ratios relative to corresponding ratios of a first reference patient having an intra-ocular PMMA lens and a second reference patient having a surgically ripe cataractous lens.

25. A method according to claim 20 further comprising:
adjusting said mixture of said second light to a third set ratio where said patient reports that third color difference dimension measures of said first and second lights appear less distinguishable; and
determining said disease state based on said first, second and third set ratios.

26. A method according to claim 20 wherein varying said mixture of said second light obtains a brightness transition range.

27. A method according to claim 20 wherein adjusting said mixture of said first light obtains a hue transition range.

28. A method according to claim 25 wherein adjusting said mixture of said second light obtains a saturation transition range.

29. A method according to claim 25 wherein said step of determining said disease state comprises interpreting a cataract condition based upon a comparison of said first, second and third set ratios and a standardization group based on age.

30. A method for determining a stage of cataract formation in an eye of a patient comprising the steps of:
providing a plurality of metameric lights for viewing by said patient, each light comprising a light mixture of at least two different wavelength components, each component having an associated luminance value;
displaying a series of predetermined proportions of associated luminance values of components of a select light of said plurality of lights;
adjusted said select light to be less distinguishable from another of said plurality of lights as reported by said patient; and
determining a stage of cataract formation based on a last portion of said series of predetermined proportions.

* * * * *

UNITED STATES PATENT AND TRADEMARK OFFICE
CERTIFICATE OF CORRECTION

PATENT NO. : 5,908,394
DATED : June 01, 1999
INVENTOR(S) : Kandel et al.

It is certified that error appears in the above-indentified patent and that said Letters Patent is hereby corrected as shown below:

ON THE TITLE PAGE:

ITEM [73] Assignee: Delete "Ronsselaer" and replace with --Rensselaer--.

Signed and Sealed this

Fifth Day of October, 1999

Q. TODD DICKINSON

Attest:

Attesting Officer

Acting Commissioner of Patents and Trademarks